US010736561B2

(12) United States Patent
Howard et al.

(10) Patent No.: US 10,736,561 B2
(45) Date of Patent: Aug. 11, 2020

(54) NEURAL MODEL-BASED CONTROLLER

(71) Applicant: HRL Laboratories, LLC, Malibu, CA (US)

(72) Inventors: Michael D. Howard, Westlake Village, CA (US); Steven W. Skorheim, Canoga Park, CA (US); Praveen K. Pilly, West Hills, CA (US)

(73) Assignee: HRL Laboratories, LLC, Malibu, CA (US)

(*) Notice: Subject to any disclaimer, the term of this patent is extended or adjusted under 35 U.S.C. 154(b) by 223 days.

(21) Appl. No.: 15/875,591

(22) Filed: Jan. 19, 2018

(65) Prior Publication Data

US 2018/0146916 A1 May 31, 2018

Related U.S. Application Data

(63) Continuation-in-part of application No. 15/682,065, filed on Aug. 21, 2017, and a continuation-in-part of
(Continued)

(51) Int. Cl.
*A61B 5/04* (2006.01)
*A61B 5/00* (2006.01)
(Continued)

(52) U.S. Cl.
CPC ........ *A61B 5/4812* (2013.01); *A61B 5/04012* (2013.01); *A61B 5/0482* (2013.01);
(Continued)

(58) Field of Classification Search
CPC .. A61N 1/36025; A61N 1/36031; A61N 1/20; A61N 1/0456; A61N 1/0476;
(Continued)

(56) References Cited

U.S. PATENT DOCUMENTS 5,722,418 A 3/1998 Bro
2012/0036099 A1 2/2012 Venkatraman et al.
(Continued)

FOREIGN PATENT DOCUMENTS

KR  10-2016-0081454  7/2016
WO  WO 03-067555  8/2003

OTHER PUBLICATIONS

Marshall L, Helgadóttir H, Mölle M, Born J. Boosting slow oscillations during sleep potentiates memory. Nature. 2006; 444(7119): pp. 610-613.
(Continued)

*Primary Examiner* — Rex R Holmes
(74) *Attorney, Agent, or Firm* — Tope-McKay & Associates

(57) ABSTRACT

Described is a system for memory improvement intervention. Based on both real-time EEG data and a neural model, the system simulates replay of a person's specific memory during a sleep state. Using the neural model, a prediction of behavioral performance of the replay of the specific memory is generated. If the prediction is below a first threshold, then using a memory enhancement intervention system, the system applies an intervention during the sleep state to improve consolidation of the specific memory. If the prediction is below a second threshold, the system reduces the intervention performed using the memory enhancement intervention system.

22 Claims, 16 Drawing Sheets

Related U.S. Application Data application No. 15/332,787, filed on Oct. 24, 2016, now Pat. No. 10,307,592.

(60) Provisional application No. 62/570,663, filed on Oct. 11, 2017, provisional application No. 62/478,020, filed on Mar. 28, 2017, provisional application No. 62/410,533, filed on Oct. 20, 2016, provisional application No. 62/245,730, filed on Oct. 23, 2015.

(51) Int. Cl.
*A61B 5/0482* (2006.01)
*A61N 1/36* (2006.01)

(52) U.S. Cl.
CPC ...... *A61N 1/36025* (2013.01); *A61N 1/36092* (2013.01); *A61N 1/36139* (2013.01)

(58) Field of Classification Search
CPC .............. A61M 21/00; A61M 2230/10; A61M 2205/52; A61M 2021/0055; A61B 5/6814; A61B 5/0476; A61B 5/4836; A61B 5/4812; A61B 5/048; A61B 5/0478; G06T 11/60; G06T 2210/41
See application file for complete search history.

(56) References Cited

U.S. PATENT DOCUMENTS

| | | |
|---|---|---|
| 2012/0184868 A1 | 7/2012 | Shaw |
| 2012/0251989 A1 | 10/2012 | Wetmore et al. |
| 2014/0051045 A1 | 2/2014 | Stiults et al. |
| 2014/0057232 A1 | 2/2014 | Wetmore et al. |
| 2016/0361541 A1 | 12/2016 | Wingeier et al. |

OTHER PUBLICATIONS

Rudoy JD, Voss JL, Westerberg CE, Paller KA. Strengthening Individual Memories by Reactivating Them During Sleep. Science. Nov. 20, 2009;326(5956): pp. 1079-1079.
Diekelmann S, Biggel S, Rasch B, Born J. Offline consolidation of memory varies with time in slow wave sleep and can be accelerated by cuing memory reactivations. Neurobiol Learn Mem. Sep. 2012; 98(2): pp. 103-111.
Rasch BH, Born J, Gais S. Combined blockade of cholinergic receptors shifts the brain from stimulus encoding to memory consolidation. J Cogn Neurosci. May 2006; 18(5): pp. 793-802.
Gais S, Born J. Low acetylcholine during slow-wave sleep is critical for declarative memory consolidation. Proc Natl Acad Sci U S A. Feb. 17, 2004; 101(7): pp. 2140-2144.
Rasch B, Buchel C, Gais S, Born J. Odor cues during slow-wave sleep prompt declarative memory consolidation. Science. 2007; 315(5817): pp. 1426-1429.
Kirov R, Weiss C, Siebner HR, Born J, Marshall L. Slow oscillation electrical brain stimulation during waking promotes EEG theta activity and memory encoding. Proc. Natl. Acad. Sci. 2009;106: pp. 15460-15465.
Jutras MJ, Fries P, Buffalo EA. Oscillatory activity in the monkey hippocampus during visual exploration and memory formation. Proc Natl Acad Sci. Aug. 6, 2013; 110(32): pp. 13144-13149.
Brincat SL, Miller EK. Frequency-specific hippocampal-prefrontal interactions during associative learning. Nat Neurosci. Apr. 2015; 18(4): pp. 576-581.
McNamara CG, Tejero-Cantero A, Trouche S, Campo-Urriza N, Dupret D. Dopaminergic neurons promote hippocampal reactivation and spatial memory persistence. Nat Neurosci. 2014 12//print; 17(12): pp. 1658-1660.
Ji D, Wilson MA. Coordinated memory replay in the visual cortex and hippocampus during sleep. Nat Neurosci. 2007; 10(1): pp. 100-107.
Kali S, Dayan P. Off-line replay maintains declarative memories in a model of hippocampal-neocortical interactions. Nat Neurosci. 2004; 7(3): pp. 286-294.
Rolls ET. Hippocampo-cortical and cortico-cortical backprojections. Hippocampus. 2000; 10: pp. 380-388.
Creutzfeldt OD, Fromm GH, Kapp H. Influence of transcortical d-c currents on cortical neuronal activity. Exp Neurol. Jun. 1962; 5: pp. 436-452.
Sederberg PB, Kahana MJ, Howard MW, Donner EJ, Madsen JR. Theta and gamma oscillations during encoding predict subsequent recall. J Neurosci Off J Soc Neurosci. Nov. 26, 2003; 23(34): pp. 10809-10814.
Osipova D, Takashima A, Oostenveld R, Fernandez G, Maris E, Jensen O. Theta and gamma oscillations predict encoding and retrieval of declarative memory. J Neurosci. 2006; 26(28): pp. 7523-7531.
Fröhlich F, McCormick DA. Endogenous electric fields may guide neocortical network activity. Neuron. Jul. 15, 2010; 67(1): pp. 129-143.
Ngo, H. V. V., Martinetz, T., Born, J., & Mölle, M. (2013). Auditory closed-loop stimulation of the sleep slow oscillation enhances memory. Neuron, 78(3), pp. 545-553.
Notification of Transmittal of International Search Report and the Written Opinion of the International Searching Authority for PCT/US2017/047865; dated Nov. 27, 2017.
International Search Report of the International Searching Authority for PCT/US2017/047865; dated Nov. 27, 2017.
Written Opinion of the International Searching Authority for PCT/US2017/047865; dated Nov. 27, 2017.
Alex Lilijecrantz, "Memory Consolidation in Artificial Neural Networks," 2 003, https://www.nada.kth.se/utbildning/grukth/exjobb/rapportlistor/2003/rapporter03/liljencrantz_axel_03148.pdf, see pp. 6-7.
Notification of Transmittal of International Search Report and the Written Opinion of the International Searching Authority for PCT/US2018/014533; dated May 10, 2018.
International Search Report of the International Searching Authority for PCT/US2018/014533; dated May 10, 2018.
Written Opinion of the International Searching Authority for PCT/US2018/014533; dated May 10, 2018.
L. Deuker, et al., "Memory Consolidation by Replay of Stimulus-Specific Neural Activity," The Journal of Neuroscience, vol. 33, No. 49, pp. 19373-19383, Dec. 4, 2013.
Rudoy JD, Voss JL, Westerberg CE, Paller KA. Strengthening Individual Memories by Reactivating Them During Sleep. Science. 2009; 326: pp. 1079-1079.
Diekelmann S, Biggel S, Rasch B, Born J. Offline consolidation of memory varies with time in slow wave sleep and can be accelerated by cuing memory reactivations. Neurobiol. Learn. Mem. 2012; 98: pp. 103-111.
Marshall L, Helgadóttir H, Mölle M, Born J. Boosting slow oscillations during sleep potentiates memory. Nature. 2006; 444: pp. 610-613.
Kato Y, Endo H, Kizuka T. Mental fatigue and impaired response processes: event-related brain potentials in a Go/NoGo task. Int. J. Psychophysiol. Off. J. Int. Organ. Psychophysiol. 2009; 72: pp. 204-211.
Henckens Mjag, Hermans EJ, Pu Z, Joëls M, Fernández G. Stressed Memories: How Acute Stress Affects Memory Formation in Humans. J. Neurosci. 2009; 29: pp. 10111-10119.
Akin M, Kurt MB, Sezgin N, Bayram M. Estimating vigilance level by using EEG and EMG signals. Neural Comput. Appl. 2007; 17: pp. 227-236.
Jaar O, Pilon M, Carrier J, Montplaisir J, Zadra A. Analysis of Slow-Wave Activity and Slow-Wave Oscillations Prior to Somnambulism. Sleep. 2010; 33: pp. 1511-1516.
Itti L, Koch C. A saliency-based search mechanism for overt and covert shifts of visual attention. Vision Res. 2000; 40: pp. 1489-1506.
Botteldooren D, DeCoensel B. The role of saliency, attentio n and source identification in soundscape research. ProcInternoise 2009

(56) References Cited

OTHER PUBLICATIONS

[Internet]. Ottowa, Canada; 2009, pp. 1-9, Available from http://citeseerx.ist.psu.edu/viewdoc/download?doi=10.1.1.468.8119&rep=rep1&type=pdf.
Lebiere C, Pirolli P, Thomson R, Paik J, Rutledge-Taylor M, Staszewski J, et al. A Functional Model of Sensemaking in a Neurocognitive Architecture. Comput. Intell. Neurosci. [Internet]. vol. 2013, pp. 1-29, Article ID 921695. Available from: http://www.hindawi.com/journals/cin/2013/921695/abs/.
Euston DR, Gruber AJ, McNaughton BL. The role of medial prefrontal cortex in memory and decision making. Neuron. 2012; 76: pp. 1057-1070.
Anderson, J. R., Bothell, D., Byrne, M. D., Douglass, S., Lebiere, C., & Qin, Y. An integrated theory of the mind. Psychological Review. 2004; 111, 4: pp. 1036-1060.
Hassabis D., Chu C., Rees G., Weiskopf N., Molyneux P.D., Maguire E.A. Decoding Neuronal Ensembles in the Human Hippocampus. Current Biology. 2009; 19(7-3): pp. 546-554.
Notification of International Preliminary Report on Patentability Chapter I for PCT/US2018/014533; dated Oct. 10, 2019.
International Preliminary Report on Patentability Chapter I for PCT/US2018/014533; dated Oct. 10, 2019.
Office Action 1 for U.S. Appl. No. 15/682,065, dated Aug. 14, 2019.
Response to Office Action 1 for U.S. Appl. No. 15/682,065, dated Dec. 13, 2019.
International Preliminary Report on Patentability Chapter II for PCT/US2017/047865; dated Nov. 15, 2018.
Notification of International Preliminary Report on Patentability Chapter I for PCT/US2017/047865; dated May 2, 2019.
International Preliminary Report on Patentability Chapter I for PCT/US2017/047865; dated May 2, 2019.
Communication pursuant to Rules 161(2) and 162 EPC for European Regional Phase Patent Application No. 17861769.2, dated May 28, 2019.
Response to the communication pursuant to Rules 161(2) and 162 EPC for European Regional Phase Patent Application No. 17861769.2, dated Dec. 6, 2019.
Correction for Chinese Patent Application No. 201780057906.9, dated Jun. 12, 2019.
Office Action 1 for U.S. Appl. No. 15/332,787, dated Sep. 18, 2018.
Response to Office Action 1 for U.S. Appl. No. 15/332,787, dated Nov. 6, 2018.
Notice of Allowance for U.S. Appl. No. 15/332,787, dated Jan. 17, 2019.

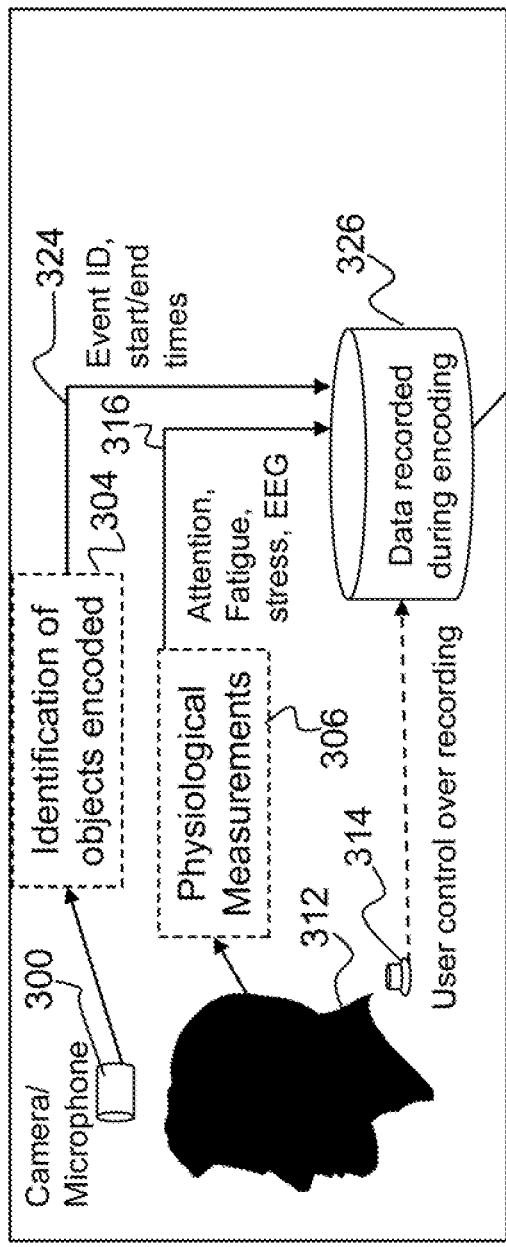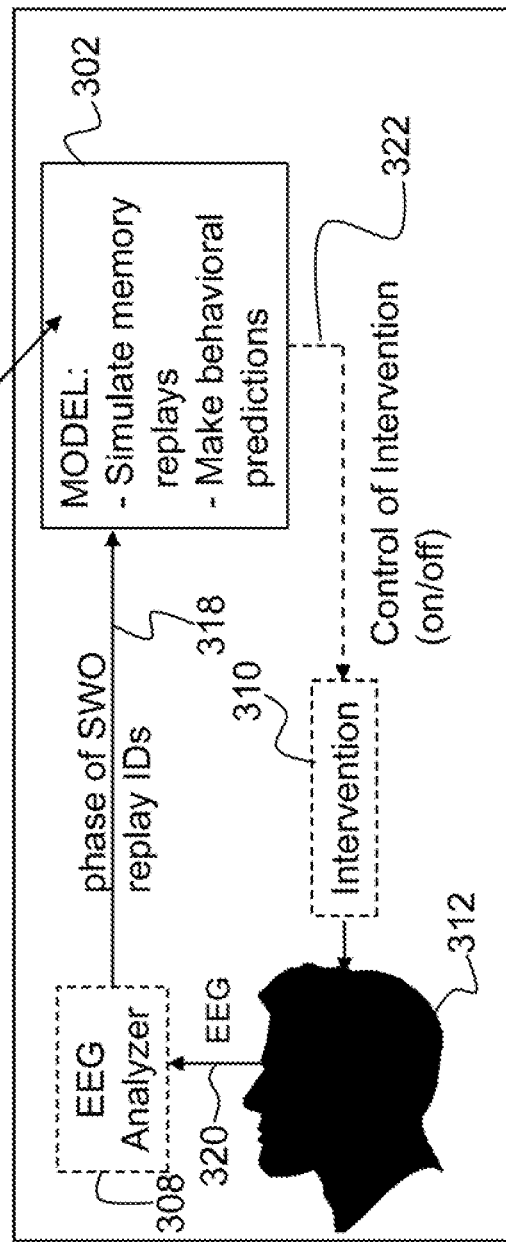
FIG. 3A
FIG. 3B

| Param | Values |
|---|---|
| $\eta$ = learning rate | $\eta$ HC=2, COR=2/40 |
| $\alpha$ = strength of inactivation current | |
| $\beta$ = strength of inhibition from other items | $\alpha$ = 0.5 |
| $\gamma$ = strength of excitation from weighted inputs to item | $\beta$ = 1.5 |
| | $\gamma$ = 20 |
| $c_a$ = activation dynamics of item | $c_a$ = 20 |
| $\tau_a$ = activation decay rate$^{-1}$ | $\tau_a$ = 0.8 |
| $\zeta$ = feedback from HC to cortex | $\zeta$ = 0.1 |
| $\lambda$ = threshold on HC feedback | $\lambda$ = 0 |
| $t_a = a_x$ threshold for self-activation to kick in | $t_a$ = .09 |
| $\delta_{a,i}$ = strength of attention on goal relevant/irrelevant items | $\delta_{a,i}$ = 0 |
| | $\delta_{a,r}$ = 0 |
| $\mu$ = strength of feedforward inputs | $\mu$ HC=2, COR=1 |

*Inactivation Current*

- $\kappa$ = dependence of inactivation current on f(x)
- $f(x)$ = *function of activation level of item x*
- $c_{xs}$ = dynamics of inactivation current
- $\theta$ = strength of inactivation current
- ex = degree of inactivation current sigmoid
- $\tau_{xs}$ = inactivation decay rate$^{-1}$

*Inactivation*

- $\kappa$ = 1
- $f(x) = a_x$
- $c_{xs} = 5*c_a$
- $\theta$ = 20
- ex = 20
- $\tau_{xs}$ =1.2

FIG. 6

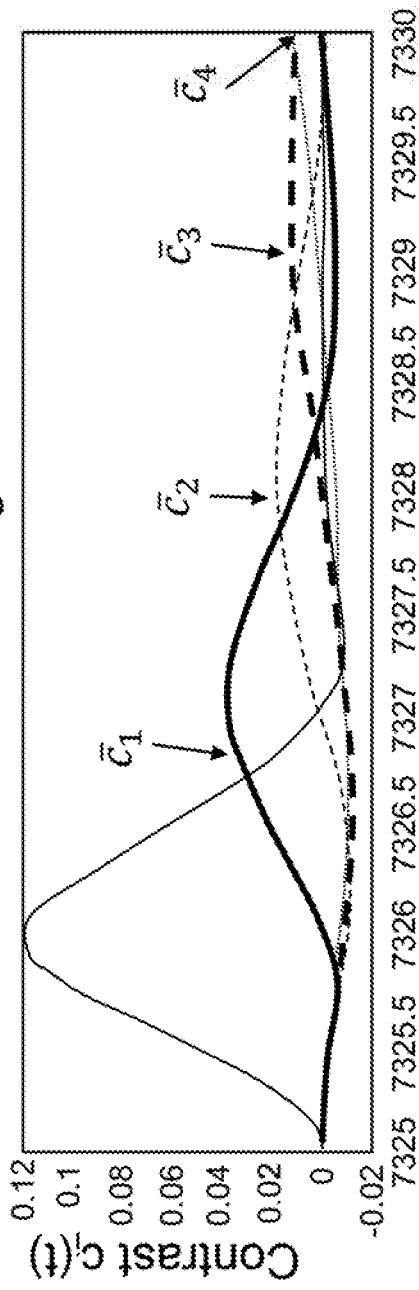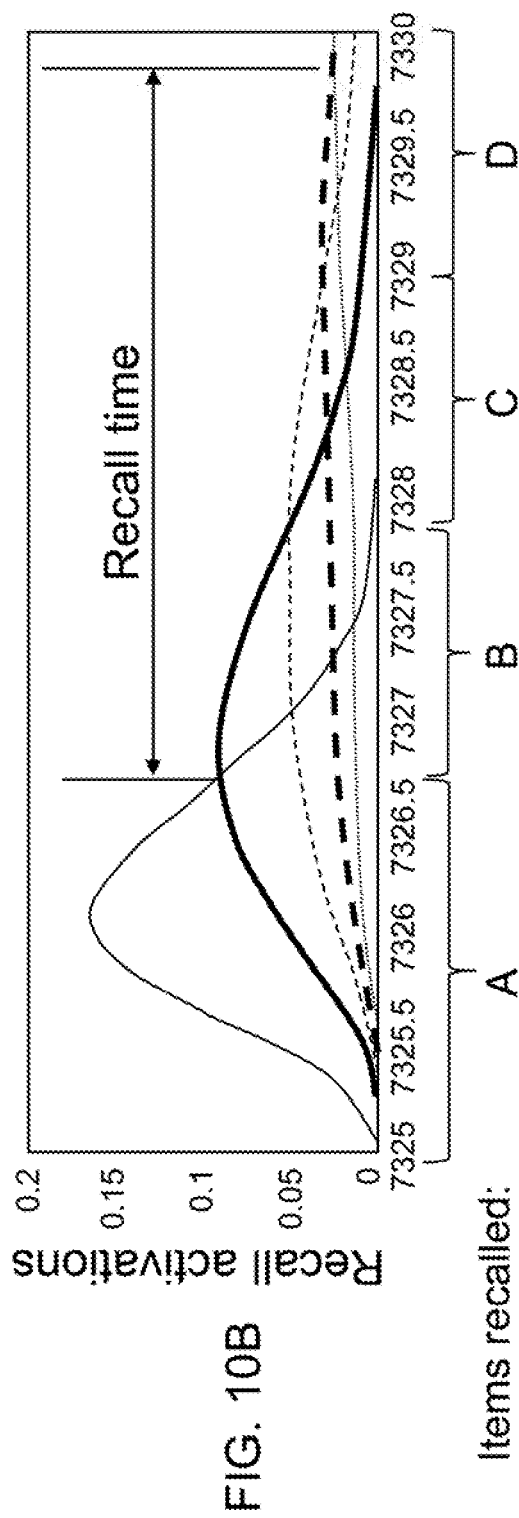
FIG. 10A
FIG. 10B

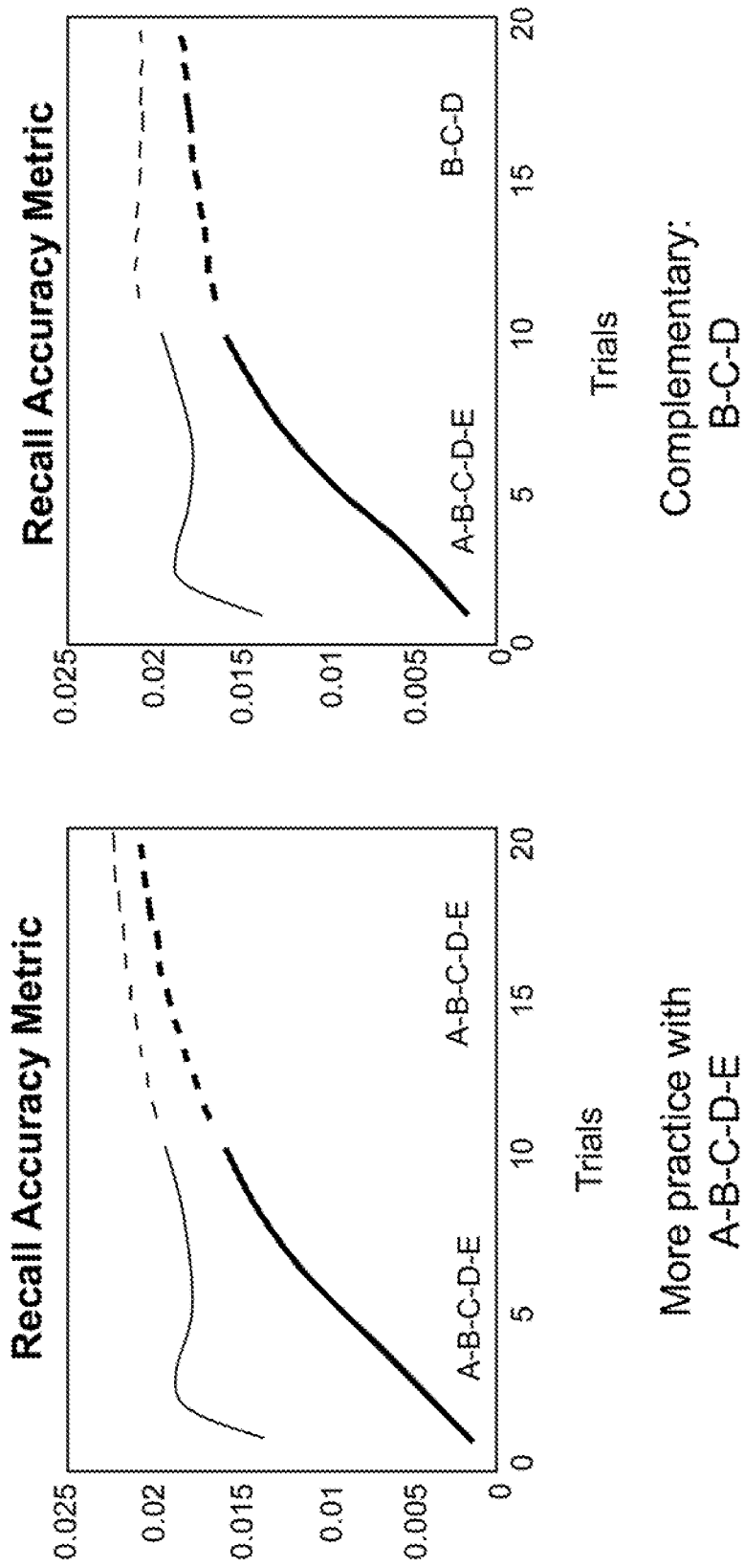

Part Complementary, Part Contradictory

Contradictory: E-D-C-B-A

NEURAL MODEL-BASED CONTROLLER

CROSS-REFERENCE TO RELATED APPLICATIONS

This is a Continuation-in-Part patent application of U.S. application Ser. No. 15/332,787, filed in the United States on Oct. 24, 2016, entitled, "Method and System to Accelerate Consolidation of Specific Memories Using Transcranial Stimulation," which is a Non-Provisional patent application of 62/245,730, filed in the United States on Oct. 23, 2015, entitled, "Method and System to Accelerate Consolidation of Specific Memories Using Transcranial Stimulation," the entirety of which are hereby incorporated by reference.

This is ALSO a Continuation-in-Part patent application of U.S. application Ser. No. 15/682,065, filed in the United States on Aug. 21, 2017, entitled, "A Closed-Loop Model-Based Controller For Accelerating Memory And Skill Acquisition, which is a Non-Provisional patent application of U.S. Provisional Application No. 62/410,533, filed in the United States on Oct. 20, 2016, entitled, "A Closed-Loop Model-Based Controller for Accelerating Memory and Skill Acquisition," the entirety of which are hereby incorporated by reference.

This is ALSO a Non-Provisional patent application of U.S. Provisional Application No. 62/570,663, filed in the United States on Oct. 11, 2017, entitled, "System and Method for Predicting Performance," the entirety of which is hereby incorporated by reference.

This is ALSO a Non-Provisional patent application of U.S. Provisional Application No. 62/478,020, filed in the United States on Mar. 28, 2017, entitled, "A Neural Model-Based Controller," the entirety of which is hereby incorporated by reference.

GOVERNMENT LICENSE RIGHTS

This invention was made with government support under U.S. Government Contract Number W911NF-16-0018. The government may have certain rights in the invention.

BACKGROUND OF INVENTION

(1) Field of Invention

The present invention relates to a system for memory improvement intervention and, more particularly, to a system for memory improvement intervention using a realistic brain model.

(2) Description of Related Art

In state-of-the-art laboratory experiments, auditory or olfactory cues are associated with memory tasks during task performance, and these cues are then used during sleep to trigger replays of that task performance memory. For instance, Rudoy (see Literature Reference No. 1 of the List of Incorporated Literature References) reported memory retention rates on object location experiments with audio cues of 97% after 1.5 hours (hrs), which can be extrapolated to 4% after 48 hrs. Additionally, Diekelman (see Literature Reference No. 2) reported 84% retention on object location experiments with odor cues after 1.67 hrs, which can be extrapolated to 5% after 10 hrs. Further, Marshall (see Literature Reference No. 3) reported 90% retention after 8.5 hrs on paired associates tasks after 10 hrs using transcranial direct current stimulation (tDCS) cues, but Marshall's technique improved every memory; it did not target specific memories.

The prior art memory intervention techniques described above were only tested in a laboratory, under supervised sleep conditions. They were never intended for real-world use; only for research on memory consolidation. ACT-R (described in Literature Reference No. 5) is a notional model of long-term memory that makes predictions about probability and speed of recall and even localization of activated neural regions in functional magnetic resonance imaging (fMRI).

Thus, a continuing need exists for a model-based intervention system for modeling long-term memory as well as short-term, with explicit modeling of the effect of sleep replays on the consolidation of short-term memories into long-term for simulating the behavior improvement possible based on the treatment given so far, online, allowing a decision of whether the intervention should be continued or should be stopped.

SUMMARY OF INVENTION

The present invention relates to a system for memory improvement intervention and, more particularly, to a system for memory improvement intervention using a realistic brain model. The system comprises one or more processors and a non-transitory computer-readable medium having executable instructions encoded thereon such that when executed, the one or more processors perform multiple operations. Based on both real-time EEG data and a neural model, the system simulates replay of a person's specific memory during a sleep state. Using the neural model, a prediction of behavioral performance of the replay of the specific memory is generated. If the prediction is below a first threshold, then using a memory enhancement intervention system, an intervention is applied during the sleep state to improve consolidation of the specific memory. If the prediction is below a second threshold, the intervention performed is reduced using the memory enhancement intervention system.

In another aspect, the system further comprises a plurality of brain sensors to provide EEG signals and the memory enhancement intervention system, wherein the neural model is part of a closed-loop control system.

In another aspect, a recall metric is used to predict behavioral performance based on strengths of memories in the neural model.

In another aspect, the prediction is applied to the recall metric, and the first threshold and second threshold are values of the recall metric.

In another aspect, the system controls intervention that applies to the specific memory such that consolidation of other memories is also allowed to occur.

In another aspect, the neural model comprises a short-term memory store and a long-term memory store, wherein each memory store comprises a plurality of items, each item having an activation level that evolves dynamically over time, wherein while an item is active, it forms links with other items that are active at the same time, wherein the links are directional to represent an order in which the linked items are experienced.

In another aspect, the links are represented as weight values, and wherein weight values are updated based on the activation levels of the linked items.

In another aspect, recall is a function of the activation level of each item, wherein an item is considered recalled if its activation level rises above the other activations going on at the same time.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where:

FIG. 3A is an illustration of data being captured for model updating during waking according to some embodiments of the present disclosure;

FIG. 3B is an illustration of the model simulating memory consolidation during sleep or quiet waking according to some embodiments of the present disclosure;

FIG. 6 is a table illustrating parameters for a neural model according to some embodiments of the present disclosure;

FIG. 10A is a plot illustrating contrast on recalled items according to some embodiments of the present disclosure;

FIG. 10B is a plot illustrating recall time on recalled items according to some embodiments of the present disclosure;

FIG. 12A is a plot of a recall accuracy metric for a more practice condition according to some embodiments of the present disclosure;

FIG. 12B is a plot of a recall accuracy metric for a complementary condition according to some embodiments of the present disclosure;

DETAILED DESCRIPTION

Figure 1:
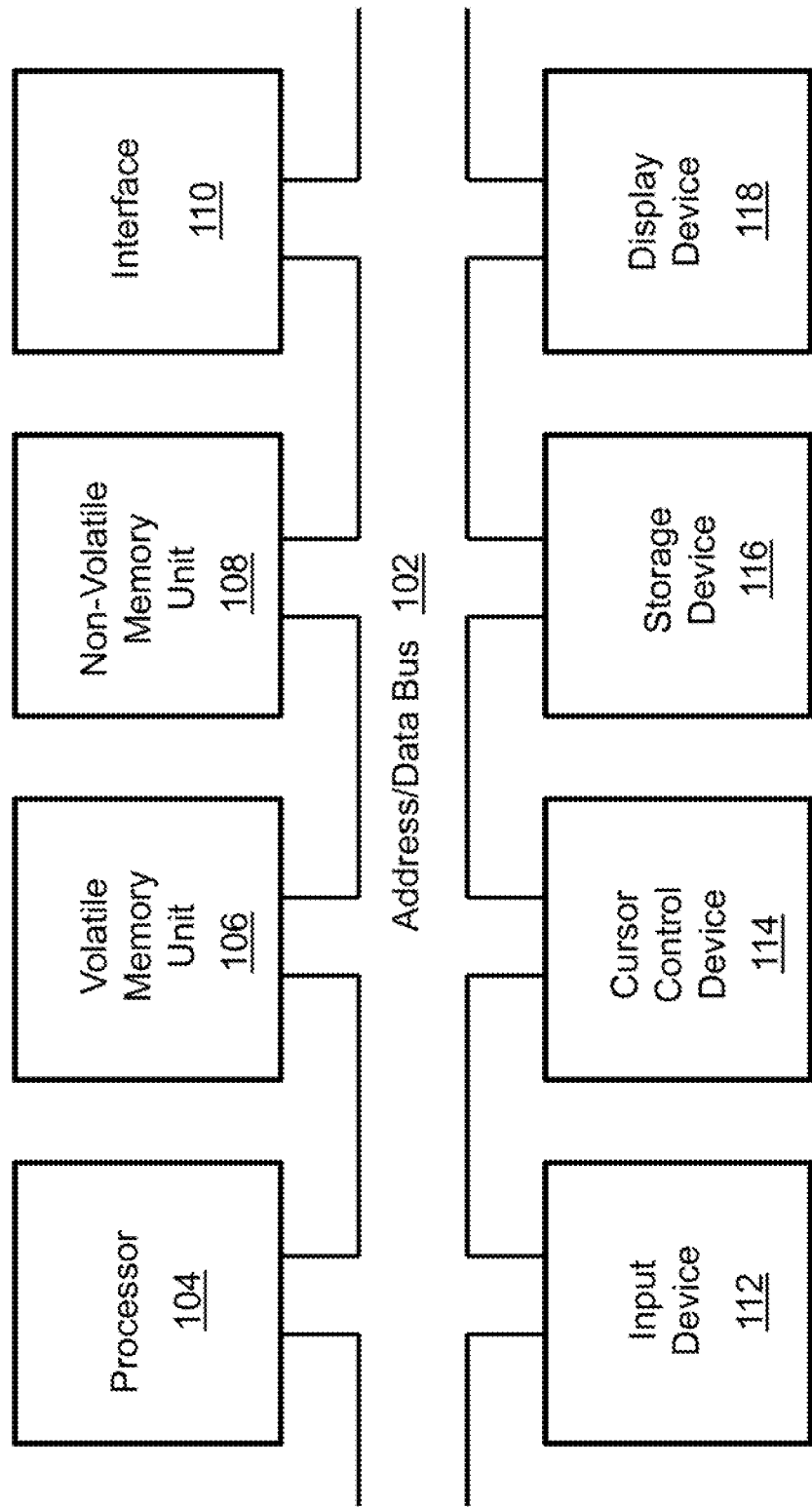
FIG. 1 is a block diagram depicting the components of a system for memory improvement intervention according to some embodiments of the present disclosure.

The present invention relates to a system for memory improvement intervention and, more particularly, to a system for memory improvement intervention using a realistic brain model. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Finally, specific details of various embodiment of the present invention are provided to give an understanding of the specific aspects.

(1) List of Incorporated Literature References

The following references are cited and incorporated throughout this application. For clarity and convenience, the references are listed herein as a central resource for the reader. The following references are hereby incorporated by reference as though fully set forth herein. The references are cited in the application by referring to the corresponding literature reference number as follows:

1. Rudoy J D, Voss J L, Westerberg C E, Paller K A. Strengthening Individual Memories by Reactivating Them During Sleep. Science. 2009; 326:1079-1079.
2. Diekelmann S, Biggel S, Rasch B, Born J. Offline consolidation of memory varies with time in slow wave sleep and can be accelerated by curing memory reactivations. Neurobiol. Learn. Mem. 2012; 98:103-111.
3. Marshall L, Helgadóttir H, Mölle M, Born J. Boosting slow oscillations during sleep potentiates memory. Nature. 2006; 444: 610-613.
4. Jaar O, Pilon M, Carrier J, Montplaisir J, Zadra A. Analysis of Slow-Wave Activity and Slow-Wave Oscillations Prior to Somnambulism. Sleep. 2010; 33:1511-1516.
5. Anderson, J. R., Bothell, D., Byrne, M. D., Douglass, S., Lebiere, C., & Qin, Y. An integrated theory of the mind. Psychological Review. 2004; 111, 4: 1036-1060.
6. Hassabis D., Chu C., Rees G., Weiskopf N., Molyneux P. D., Maguire E. A. Decoding Neuronal Ensembles in the Human Hippocampus. Current Biology. 2009; 19(7-3): 546-554.

(2) Principal Aspects

Various embodiments of the invention include three "principal" aspects. The first is a system for memory improvement intervention. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
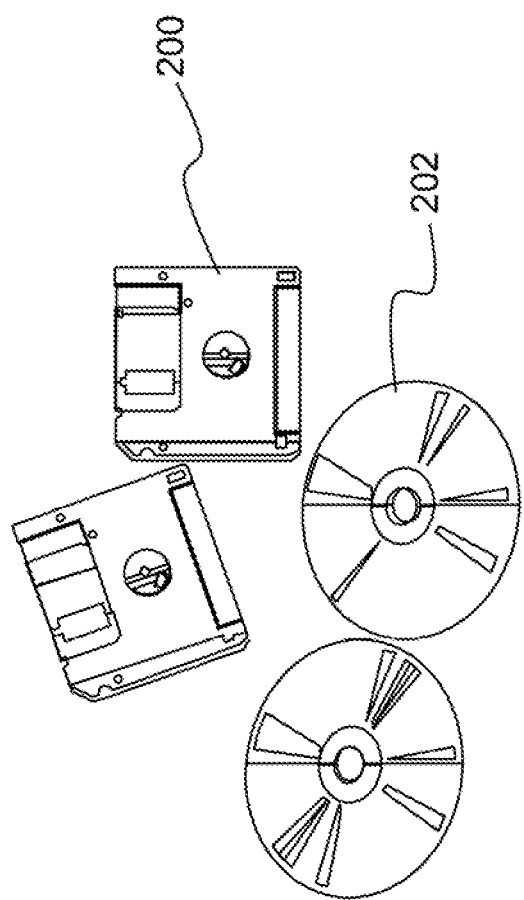
FIG. 2 is an illustration of a computer program product according to some embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Specific Details of Various Embodiments

Described is a detailed model of the way that humans learn new sequences of actions and skills. Specifically, the model is in terms of how the representations in the brain are initially encoded into connections between ensembles in volatile short-term memory in the hippocampus, and then gradually get consolidated into more stable and persistent connections in the cortex. This model expands upon one disclosed as part of a closed-loop model-based control system in U.S. Non-Provisional application Ser. No. 15/682, 065 (hereinafter referred to as the '065 application), which is hereby incorporated by reference as though fully set forth herein. The model described herein is critical for coordinating with natural consolidation processes to avoid unnecessary interventions by prioritizing skills predicted to perform below desired levels (e.g., memories of specific things that must be learned quickly and remembered clearly and easily).

The model described herein simulates, at a detailed neural ensemble level, the encoding and consolidation of memories, and makes predictions of the resulting behavioral performance (i.e., the subsequent ability to recall and use memories of interest). Used in a control loop with brain sensors and the intervention system, this model turns on the intervention when the behavioral predictions are below a desired level (e.g., a first threshold), and turns it off when behavioral predictions surpass a threshold of performance (e.g., a second threshold). The first threshold and second threshold may be the same or different. Since there are many memories that need to be consolidated during the night, an intervention to improve one specific memory must not prevent consolidation of other memories; this is one benefit of the model-based controller according to embodiments of the present disclosure. Importantly, the model updates its representations and makes new predictions very quickly and efficiently. Such a control system for a memory improvement intervention, using a realistic brain model to decide when interventions are needed during sleep, has never been conceived.

The model-based controller (elements 302 and 322) is the software memory simulation that runs on a processor and predicts the behavioral performance level related to a specific memory. Note that the intervention module (element 310) associates a cue with a memory during waking. However, then during sleep, it must apply that cue to promote replays of the memory during slow-wave-sleep. Without the invention described herein, the intervention is applied blindly; there is no way to know whether the memory is sufficiently consolidated to get the desired level of performance. When the intervention is operating, other memories (e.g., people the user has met, things the user has learned) can't be consolidated. Therefore, the system according to embodiments of the present disclosure predicts when the user has sufficiently consolidated the memory of interest, and then stops the intervention so the user can consolidate other memories.

In operational tasks (as in many business and educational scenarios), it can be critically important to quickly integrate new information (based on limited exposure) and accurately recall it. The purpose of the invention described herein is to control interventions that enhance memory consolidation to make this possible. It is widely accepted that memories are consolidated during sleep, and a few prior art laboratory experiments have implemented some targeted interventions. However, the system according to embodiments of the present disclosure is the first to implement a control loop around an intervention in order to control exactly when an intervention should be applied in order to achieve the desired level of performance.

The invention will automatically determine if and when certain interventions should be applied during sleep and quiet waking periods. The system does this by predicting behavioral performance outcomes resulting from memory replay activity during quiet waking or slow wave sleep (within the 0.5-1.2 Hertz (Hz) frequency band of slow wave oscillations), thereby allowing selection of the best replay intervention options to achieve a desired performance. When the predicted performance reaches a desired level, the model turns off the interventions, allowing other memories to be consolidated. The model is shaped by the sequence and content of all experienced stimuli in a situation paradigm, as well as the characteristics of prior replay events. Thus, it can predict the impact that further intervention will have on behavior. Without the control system described herein, the interventions during sleep to improve consolidation of a specific memory or memories are uninformed, because there is no way to get feedback on behavioral performance until the subject wakes up and is tested. If the interventions are applied more than necessary, it prevents other memories from being consolidated and can even cause deterioration of the memory the intervention is attempting to reinforce. If the interventions are applied less than necessary, the desired behavioral performance will not be achieved.

There are many uses for such a detailed personalized model of human learning and retention of learning. The model can be used to inform any training system as to how well an individual subject is learning. Additionally, the model can be utilized to predict behavioral performance gains resulting from further exposure to training and determine how well a particular skill or memory is consolidated during sleep. Further, the model could be used to estimate how current skills and memories decay as a result of encountering interfering skills or memories, which can be used as a proactive tool to interfere with undesirable memories or bad habits. In addition, it can be utilized to simulate the effects of lack of sleep in an individual.

The concept behind the invention described herein is based on the widely accepted and well-supported idea that new memories are first encoded as connections in short-term memory in the human brain's hippocampal region. Then, gradually over a period of days, weeks, or months, they are consolidated into a slower-learning, more stable, brain region known as cortex in which long term memories are stored. Once information is consolidated into long-term memory, it becomes more resistant to decay. This consolidation process involves events called "replays" that occur during a deep stage of sleep called slow-wave sleep during non-rapid-eye-movement sleep (NREM). The theory holds that the more often a memory is replayed, the better a person performs when tested on a behavior dependent on recall of that memory. Although any memory in the short-term store has a chance of being replayed during sleep, there is a higher probability that a specific memory will be replayed if it was related to some emotional content or high immediate reward. Unfortunately, many things humans need to learn are boring or tedious, and the reward for learning them may be a long way off. This is the motivation behind memory interventions. Accordingly, the system according to embodiments of the present disclosure is an automation technique—an intervention control system that will improve the effectiveness and efficiency of any of these interventions that produce replay of specific memories.

The model described herein models the way the human brain encodes and consolidates memories of events and skills during waking experience and sleep. The model is personalized to simulate a particular individual subject based on biometric data from the subject. There are surely many uses for such a model, but one implementation is to use it to predict how well a particular person can recall a specific sequence of inputs. When the prediction is above the threshold for the desired level of performance, the model sends a signal to control an intervention to improve the memory or skill. That is, the intervention is actively applied until the performance predictions exceed the desired level, and then the intervention is turned off.

The current invention describes a design for a neural model that can make accurate behavioral predictions. The model according to embodiments of the present disclosure quantitatively simulates the impact of sleep on long-term memory function and teases apart equally important contributions from waking encoding in short-term memory and sleep consolidation in long-term memory. Speed and efficiency can be critically important for interventions, such as the implementation described above, that decide how to intervene on every positive phase of the slow-wave sleep oscillation (SWO) during the deepest stage of sleep (NREM sleep stages 3 and 4). There are a limited number of these oscillations during a night of sleeping (SWOs are at a frequency of 0.5-1.2 Hz for often much less than 90 minutes of a night's sleep), and the EEG analysis of the dynamically changing SWO frequency and recognition of the identity of a replay takes time before the model can simulate the results. Therefore, it is desirable for the model to make behavioral predictions well within 100 milliseconds (ms) after a reported memory replay during the average 500 ms time between the positive phases of SWO to control memory interventions during the next positive phase of SWO. The model's subject-specific predictive power in the context of task performance comes from simulating non-invasively assessed markers of attention during encoding as well as the duration and quality of consolidation periods.

(3.1) Basic Architectural Diagram

FIGS. 3A and 3B illustrate the basic architecture of the entire system described herein. During waking (e.g., a higher activity state) (FIG. 3A), data is captured (via a camera and/or microphone 300) for model 302 updating, and during sleep or quiet waking (e.g., a lower activity state) (FIG. 3B), the model 302 simulates memory consolidation. The model 302 simulates behavioral performance and controls when to apply the intervention. Operations/modules in dashed lines (identification of objects encoded 304; physiological measurements 306; EEG analyzer 308; intervention 310) are prior art.

During a waking experience (FIG. 3A), when a user 312 is about to experience an event that must be remembered accurately, data recording is initiated either by some automated decision system or by the user 312, such as via a button 314 that initiates recording. Prior art systems identify the percepts that are most salient to the subject at that time (i.e., identification of objects encoded 304).

For visual items, an eye tracker can be used to decide what the user 312 is looking at (e.g., an image chip is formed around visual fixations averaged over a short (1 second) time window). Alternatively, the user 312 can actually take a static picture of the item of interest. These images can be identified using an open-source system, such as ImageNet/GoogleNet, to provide a semantic symbol that identifies the object. For speech recognition, there are many known systems that are can recognize speech. Physiological measurements 306 are made by analyzing electroencephalograms (EEG), electromyograms (EMG), and electrocardiograms (ECG) based on biometric sensor data from the user 312. Mental fatigue significantly modulates the amplitude of certain event-related potentials (ERPs), and stress can be inferred from ECG read-outs of heart rate variability. A small amount of stress can improve encoding strength, but higher levels of stress interfere with encoding. Attention, or vigilance, can be estimated from EEG and EMG (element 316).

In FIG. 3B, the intervention module (element 310) is a prior art system (described in U.S. application Ser. No. 15/332,787, hereinafter referred to as the '787 application, which is hereby incorporated by reference as though fully set forth herein). The system described in the '787 application associates a cue like an odor (see, for example, Literature Reference No. 2), a sound (see, for example, Literature Reference No. 1), or electrical stimulation with the memory of interest during waking, and reapplies it during sleep or quiet waking as a cue to trigger a recall of the specific cued memory. The intervention module (element 310) is also referred to as a memory enhancement system. Later, the cue can be replayed to cue the memory during sleep, consolidating the memory from short term to long term memory.

The EEG analyzer module (element 308) is a prior art module that can detect the sleep stage 318, including detection of slow wave oscillations (SWOs). SWOs occur mostly during the deepest stages of sleep (NREM stage 3 and 4), although they can occur during times of deep restfulness in a quiet waking state as well. Sleep stages are detectable by commercial sleep monitors. The phase of SWO can be ascertained currently by analysis of the EEG signal 320. An automated analysis system is not commercially available, but the methods for EEG signal analysis are known to those skilled to the art (see Literature Reference No. 4). The model 302 simulates the replay of memories during sleep and predicts the behavioral results of such replay. Based on the model 302's prediction, the intervention may be controlled 322 on or off. The model 302, which is the subject of this disclosure, is described in detail below. The model-based controller can turn the intervention on and off (element 322) all night long as the subject sleeps. If a memory is fully consolidated and the intervention is turned off, the memory may decay as other, possibly conflicting memories, are replayed during sleep. In this situation, the system would turn the intervention on again.

(3.2) Neural Memory Computational Model

Figure 4:
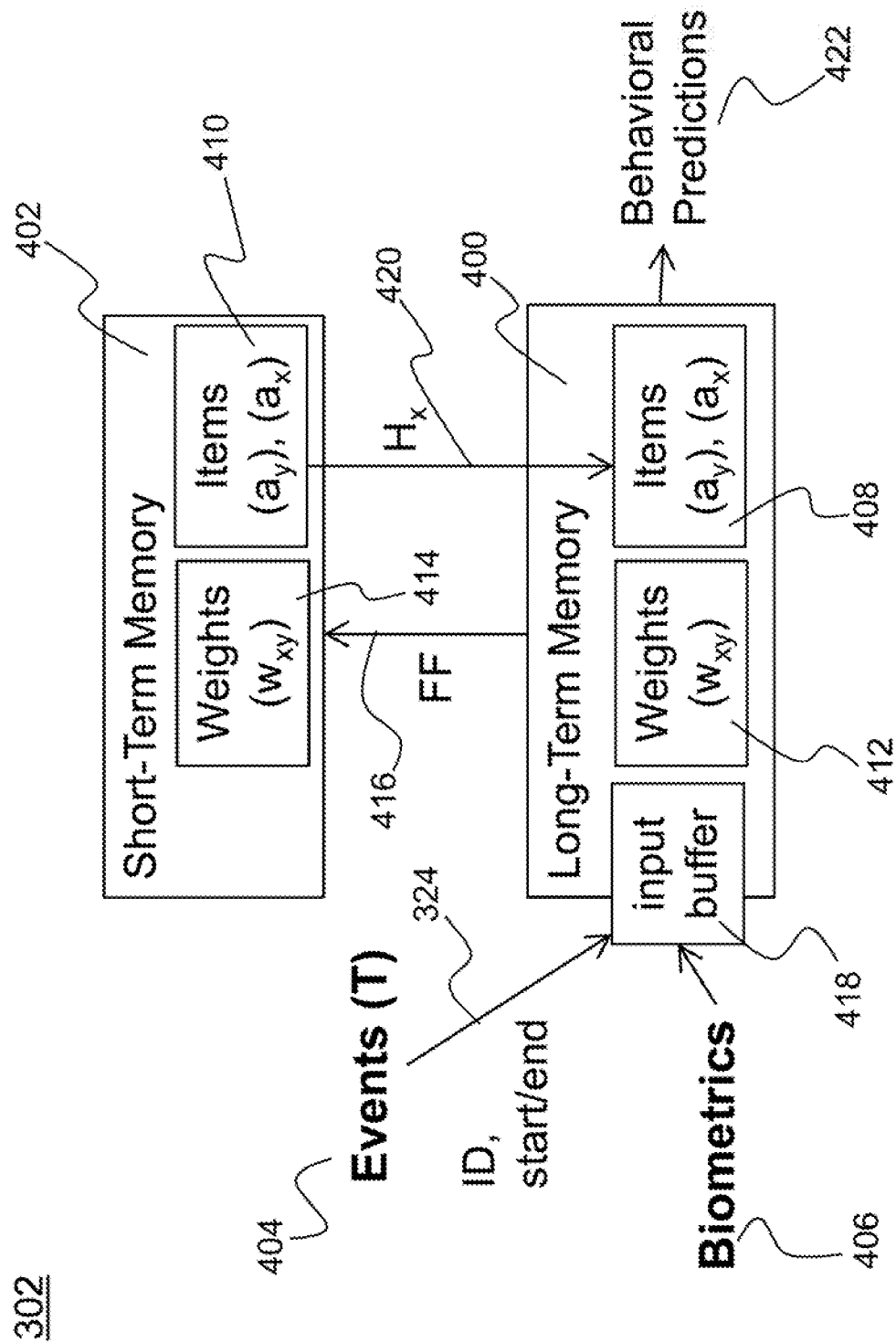
FIG. 4 is an illustration of the neural memory model simulating encoding, decay, consolidation, and recall of novel multi-modal experiences and knowledge in real-world environments according to some embodiments of the present disclosure.
Figure 5:
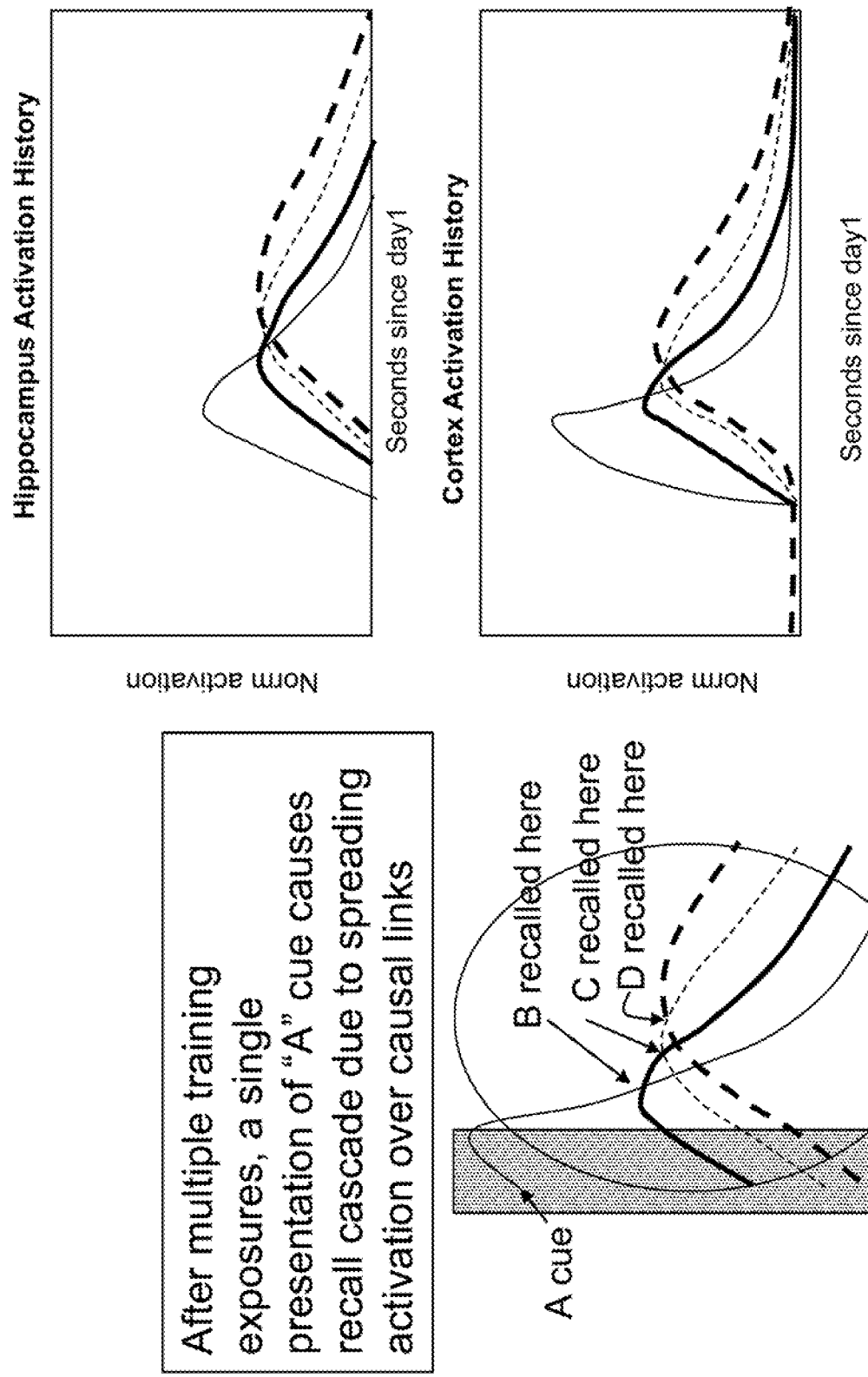
FIG. 5 is an illustration of a cued recall cascade according to some embodiments of the present disclosure.

The neural model 302 according to embodiments of this disclosure is depicted in FIG. 4. The neural memory model 302 described in this disclosure simulates encoding, decay, consolidation, and recall of novel multi-modal experiences and knowledge in real-world environments. The main modules of the model are a short-term memory store 400 and a long-term memory store 402. During waking (FIG. 3A), a sensory event is identified with a unique ID, as well as a start and end time 324, and is given as a training input (T) 404 to identify each relevant experience (both task related and distractions or interfering experiences). Both the event ID, start/end times 324, and attention, fatigue, and stress measurements 316 are recorded and stored during encoding 326, as shown in FIG. 3A. As depicted in FIG. 4, biometrics 406 are reported by the physiological measurements module 306 of FIG. 3A, in terms of levels of attention (a), mental fatigue (m), and stress (s) during the training period.

During sleep, EEG signals 320 are analyzed. During the slow-wave sleep stage, the start and end time of each positive phase is reported to the model 302, along with a probability distribution across specific memory events that may have been replayed during that time period. The model 302 is not specific to the type of skill being learned and can be easily adapted to a number of tasks.

In the following, the term "skill" is used to describe a memory, possibly associated with actions, such as how to assemble a complex piece of equipment, or what happened during a mission for later debrief. The model 302 represents the user's ability to recall that skill quickly and easily in terms of the strength of integration with other memories in both short term (STM) memory 400 and long term (LTM) memory 402. The idea that memories are represented by the level of spiking activity of an ensemble of neurons in the brain is widely accepted (see Literature Reference No. 6). The activation level of an item in short term memory is ephemeral and dies down soon after the item is experienced or recalled. However, while an item is active, it forms links with other items that are active at the same time. These links are directional to represent the order in which the linked events are experienced. In STM 400, both the item activations and their links to other items change on the order of minutes to hours, whereas in LTM 402, they change slowly, on the order of days to years. This is the reason why memories encoded quickly in STM 400 must be transferred to LTM 402. This transfer is called consolidation, and the invention described herein models this process more thoroughly than any model to date.

There are several ways of modeling of the interaction between memories in the dual-store system (elements 400 and 402) described. The invention includes an adaptive cortico-hippocampal architecture that accounts for emergent sleep replays underlying the transfer of long-term memory/skill representation from hippocampus to neocortex. The following set of equations is one implementation, but there are many roughly equivalent ways to express the sort of dynamical relationships between memories. The user's interactions with each skill are called either training or testing. The difference is that training, which could be a formal pedagogical training session with an instructor, provides feedback. Testing, or simply experiences in the environment, provides no feedback. The neural model 302 according to embodiments of the present disclosure is defined by three equations: a pair of differential equations (1) and (2) that govern the item activation updates (elements 408 and 410 in FIG. 4), and a weight update (elements 412 and 414 in FIG. 4) equation (3). Item activations ($a_X$ represents the activation of item X) evolve dynamically over time as follows:

$$\sigma c_a \frac{da_X}{dt} = -\frac{a_X}{\tau_a} - a_X \left[ \beta \sum_{Y \neq X} a_Y + \frac{\Theta x_s^{ex}}{x_s^{ex} + t_{xs}^{ex}} \right] + \quad (1)$$

$$(1 - a_X) \left[ \mu \cdot FF + \gamma \sum_{Y \neq X} w_{YX} a_Y + \frac{\alpha a_X^{ex}}{a_X^{ex} + t_a^{ex}} + \zeta [H_X - \lambda]^+ \right]$$

The table in FIG. 6 lists the meaning of each variable and some default values. The $x_s$ variable is an "inactivation current" modeled after ion channel dynamics. $X_s$ evolves at a slower rate than $a_X$, and increases inhibition on the item activation when it gets large.

$$\sigma_s c_{xs} \frac{dx_s}{dt} = -\frac{x_s}{\tau_{xs}} + (1 - x_s)[\kappa f(x)], \; c_{xs} > c \quad (2)$$

In the model 302 described herein, these relational links are represented as weight values. Weight updates (elements 412 and 414) are based on the activation (elements 408 and 410) of the pre-synaptic item and the derivative of the activation of the post-synaptic item, which learn casual connections for the spreading activation by means of equation (3).

$$\frac{dw_{XY}}{dt} = \eta a_X (1 - w_{XY}) \left[ \left[ \frac{da_Y}{dt} \right]^+ - \frac{1}{2} \left[ -\frac{da_Y}{dt} \right]^+ \right] \quad (3)$$

$$f(biometricFactors) f(distractionFactor)$$

Cell and inactivation current dynamics are scaled by a factor $f$. Other variables are shown in the table in FIG. 6.

Equation (1) updates the activation value of each item x by subtracting a decay term and an inhibitory term, and adding an excitatory term. The inhibitory current is a function $a_X[\beta E_{Y \neq X} a_Y + \Theta f(x_s)]$. $\beta$ is an inhibition parameter, and the sum of $a_Y$ provides competition from other items. $x_s$ is a slow variable undated in equation (2) with a dynamics speed variable $\sigma_s \ll \sigma$, where $\Theta$ is a parameter and $f(x_s)$ is sigmoid $$\frac{x_s^{ex}}{x_s^{ex} + t_{xs}^{ex}}$$

to smoothly bound the values. $T_{xs}$ is a threshold for the $x_s$ value at the point, where the sigmoid value is half of its maximum value, and ex is an exponent controlling the steepness of the sigmoid rise.

The excitatory current is a function of feed-forward excitation FF (element 416) and a weighted sum of inputs from activated items linked to item x. For STM 402, FF (element 416) is the activation of items in the input buffer 418 exciting their representations in the STM 402. For LTM 400, FF (element 416) is the activation of the corresponding item in STM 402, and the factor $\zeta([H_X - \lambda]^+$ (element 420) is a feedback excitation from STM to LTM, subject to a threshold parameter A. For the hippocampus, $\zeta = 0.1$. $(1-a_X)$ is reversal potential, which is a homeostasis term that means that if $a_x$ overshoots the maximum value of 1, the spreading activation from other items becomes a negative term, thereby reducing the value of $a_x$.

$\gamma \Sigma_{Y \neq X} W_{YX} a_Y$ spreads activation to $a_x$ (elements 408 and 410) as a function of the weighted sum of activations of items Y that are directionally linked to item X by weight $W_{yx}$ (elements 412 and 414). Activation is spread within items in each memory region. $\gamma$ is a tuning parameter that defaults to 0.4.

$$\frac{\alpha a_X^{ex}}{a_X^{ex} + t_{xs}^{ex}}$$

is a self-excitation term to accelerate the increase in activation, but it is a sigmoid form that does not increase the activation of $a_x$ beyond the value of the multiplier $\alpha$, which defaults to 0.5.

Learning occurs through the change of weights between active items as described in equation (3). All weights are initialized at 0 and can never be negative. The learning rate, $\eta$ is a constant that scales how quickly the model learns in all situations. Higher learning rates allow more rapid integration of information but also increase the likelihood that random events will be learned along with the more meaningful stable patterns. The change in weight of the connection from item x to item y includes a factor of $(1 - w_{XY})$ which will cause the rate of weight change to reduce as the weight approaches 1 and sets 1 as the maximum obtainable weight. The weight of the connection between x and y changes whenever the activity of x $(a_X)$ is not 0, and the activity of item y $(a_y)$ is not constant. Weight change is directly proportional to the activity of x $(a_x)$ and proportional to the rate of change in the activity of y $(da_Y)$. If $(da_Y)$ is negative, the weight change is reduced by half. This is necessary for the learning of connections between simultaneous events.

The dependency of the weight upon the activity of the presynaptic ensemble (item x) and the rate of change in the activity of the post synaptic ensemble (item y) creates a type of Hebbian plasticity. In Hebbian theory, as in the model described herein, if activation of item x reliably increases the activity in item y, the connection from x to y increases in strength. If the activity in item y declines despite strong input from item x, indicating that the ensemble associated with x is ineffective at activating the ensemble associated with y, the connection is reduced in strength. When items are activated in succession, the first item will still be active when the second item's activity begins to rise; this results in an increase in the strength of their connection. If the first item has already reached the peak of its activation by the time the next item begins activating, the resulting changes in weight in the reverse direction (from y to x) will be negative. The model 302 described herein incorporates the effects (physical or psychological factors) that can be observed in the subject's biometric data (element 406). Lack of attention, stress level, or fatigue can all have an impact on learning. Introduction of task irrelevant distractors can also play a part. This is represented by the factor $f$(biometrics) in equation (3), as described below in equations (4) and (5).

(3.3) Personalization: Biometric and Distraction Factors

The neural memory model 302 described above is personalized by incorporating biometrics 406 measured by prior art techniques, including measurements of the subject's fatigue, stress, and attention during waking. These inputs are used to modulate the initial activation level of the memories when they are learned or trained (i.e., the time of memory encoding). At times other than task-relevant training and testing, biometric parameters identify memory-relevant physiological states and replay parameters that change the model's mode of operation during periods of waking, quiet waking, and the stages of sleep.

Figure 7:
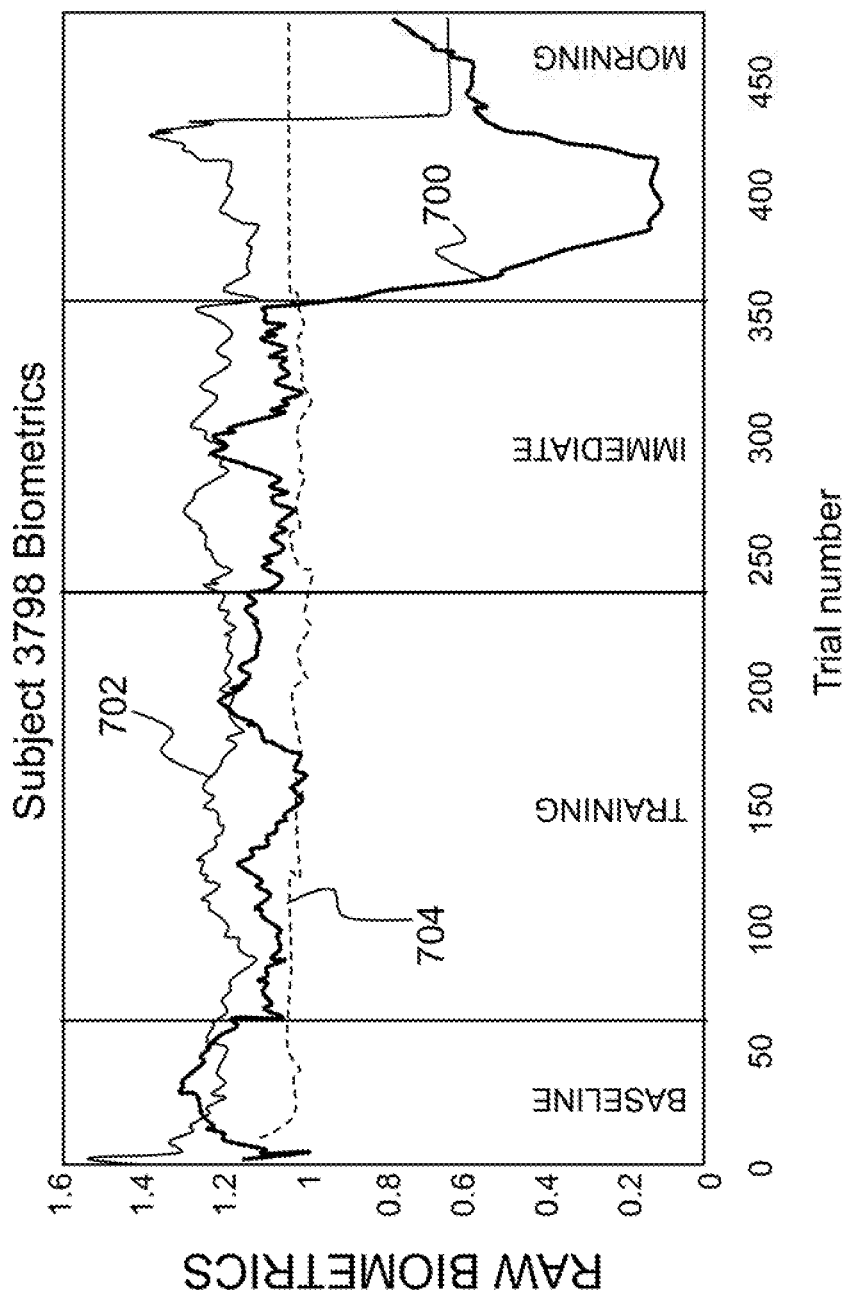
FIG. 7 is a plot illustrating raw biometric values for fatigue, stress, and attention extracted from an electroencephalogram subject according to some embodiments of the present disclosure.

In one embodiment, three biometrics 406 are extracted from EEG using prior art techniques, including mental fatigue, stress, and attention. Raw biometric values for fatigue, stress, and attention are shown in FIG. 7 as extracted from EEG from subject 3798 in a pilot task. The values range from 0 to 2. Baseline is an acclimation period trials 0-60. Task training was trials 61-240, and the immediate test was right after training. Biometrics were fairly flat through the first day training and testing (to trial 355), but in the morning tests (trials 356-475 after sleeping) the fatigue metric (bold line 700) is significantly lower. The plot in FIG. 7 shows that mental fatigue (bold line 700) is significantly reduced after sleep. The solid, unbolded line 702 represents attention, and the dashed line 704 represents stress.

Figure 8:
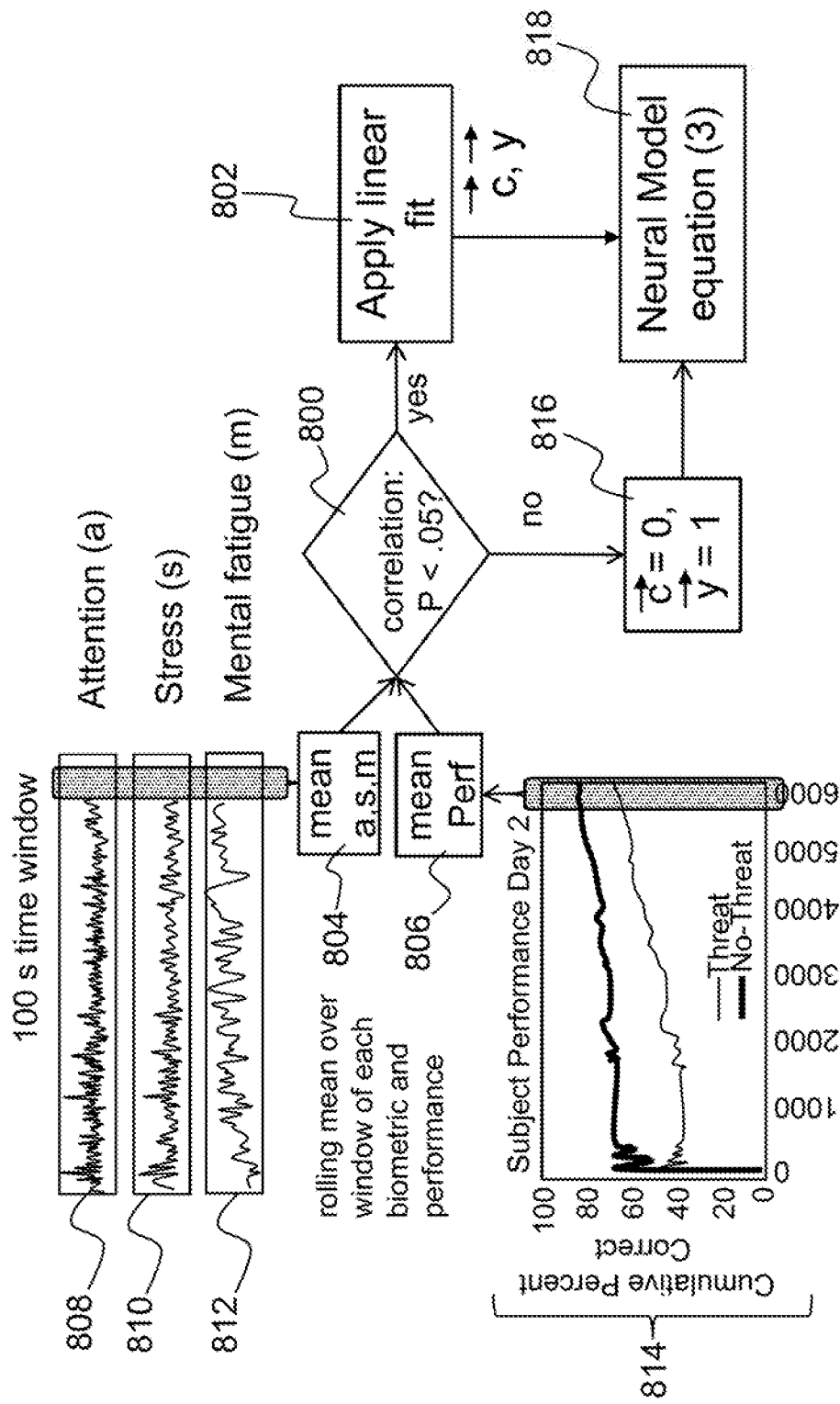
FIG. 8 is an illustration of determining modulation parameters for biometric influence on model predictions according to some embodiments of the present disclosure.

FIG. 8 depicts a method of determining modulation parameters for biometric influence on model predictions (i.e., behavioral predictions 422 in FIG. 4) according to embodiments of the present disclosure. Only biometrics significantly correlated with performance are used in the model 302. The effect of biometrics on the model simulation is modulated by the amount of correlation 800 between each biometric value and the subject's performance. An online update method according to embodiments of the present disclosure is based on degree of correlation 800 with performance (using linear fit parameters for significant correlations (i.e., apply linear fit 802)). The biometric influence is updated every m trials (currently m=1). A rolling mean of each biometric (mean a (attention), s (stress), f (fatigue) 804) and subject behavioral performance metric (mean perf 806) is computed in a temporal window (e.g., 100 seconds). Each biometric (e.g., attention 808, stress 810, mental fatigue 812) is correlated (element 800) with each performance metric (element 814) and only incorporated into the cognitive model for periods when the correlation 800 is significant (e.g., where the p-value is <0.05). Equation (4) below shows the biometric factors shown in equation (3) for the cognitive model's update to the short-term memory level $E_x$.

$$\text{biometric\_factors} = (c_a A + y_a)(c_m M + y_m)(c_s S + y_s) \quad (4)$$

Here A, M, and S represent attention factor, mental fatigue factor, and stress factor (each adjusted to −1 to 1 range by subtracting 1), respectively. $\vec{C}_*$ is a vector of parameters that modulate the impact of the respective biometric. If the correlation 800 for a biometric is not significant, the $\vec{C}_*$ parameter is set to 0 for that biometric, and the corresponding $\vec{Y}_*$ is set to 1 (element 816). However, if the correlation 800 is significant for a certain time period, a first-order linear fit 802 is used to find a slope and intercept of a regression line that relates the biometric to the performance. For example, a MATLAB implementation of such a linear fit 802 uses the function polyfit as follows:

[c,y]=polyfit(biometric_vector, matching_performance vector, 1).

Equation (4) incorporates the correlation between attention (a metric extracted from EEG by a prior an method) and performance. However, there are also externally observable indications of distraction, such as the gaze moving to task irrelevant areas of the field-of-view, or physical body orientation (e.g., orientation of head and/or arms) in a task irrelevant manner. These indications can be incorporated into equation (3) if it makes sense for the task being modeled (element 818). A non-limiting example is a surveillance task in which the subject has to take pictures of people that appear in the windows of a building. If a distraction occurs in one of the windows, such as a dog running across the room, and the subject takes a picture of it by mistake, then the subject's action (taking the picture) is an external indication that the subject was distracted by the dog. In Equation (5) below, D is a binary signal that is 1 when any distractor is present, and 0 when no distractor is present. $Y_d$ is a modulation parameter for the strength of the distraction factor (e.g., $y_d$=0.00005), and d is a modulation parameter for the interaction (e.g., d=1). The interaction variable is a binary value that goes to 1 if there is interaction with the distractor and is otherwise 0. The prefixed ($T_x(x)>0$) factor provides that the distraction factor is only used for a skill x that is currently active, which is when training happens and Tx>0.

$$\text{distraction\_factor} = (T_x(x)>0) * (y_d*(D>0) + d*\text{interaction}) \quad (5)$$

(3.4) Simulation of Memory/Skill Consolidation During Sleep

In the brain, the fast-learning, fast-decaying hippocampus (simulated by the short-term memory 400 described herein) must train the slow-learning cortex (simulated by the long-term memory 402 described herein) (shown in FIG. 4). During slow-wave sleep, salient memories can become randomly reactivated in short-term memory 400, driving replays in the long-term memory 402 and strengthening the long-term connections. These reactivated memories are called emergent replays. After a sufficient number of replays, hippocampal connections are no longer needed to drive the spread of activation along learned links when an item is activated.

Figure 9:
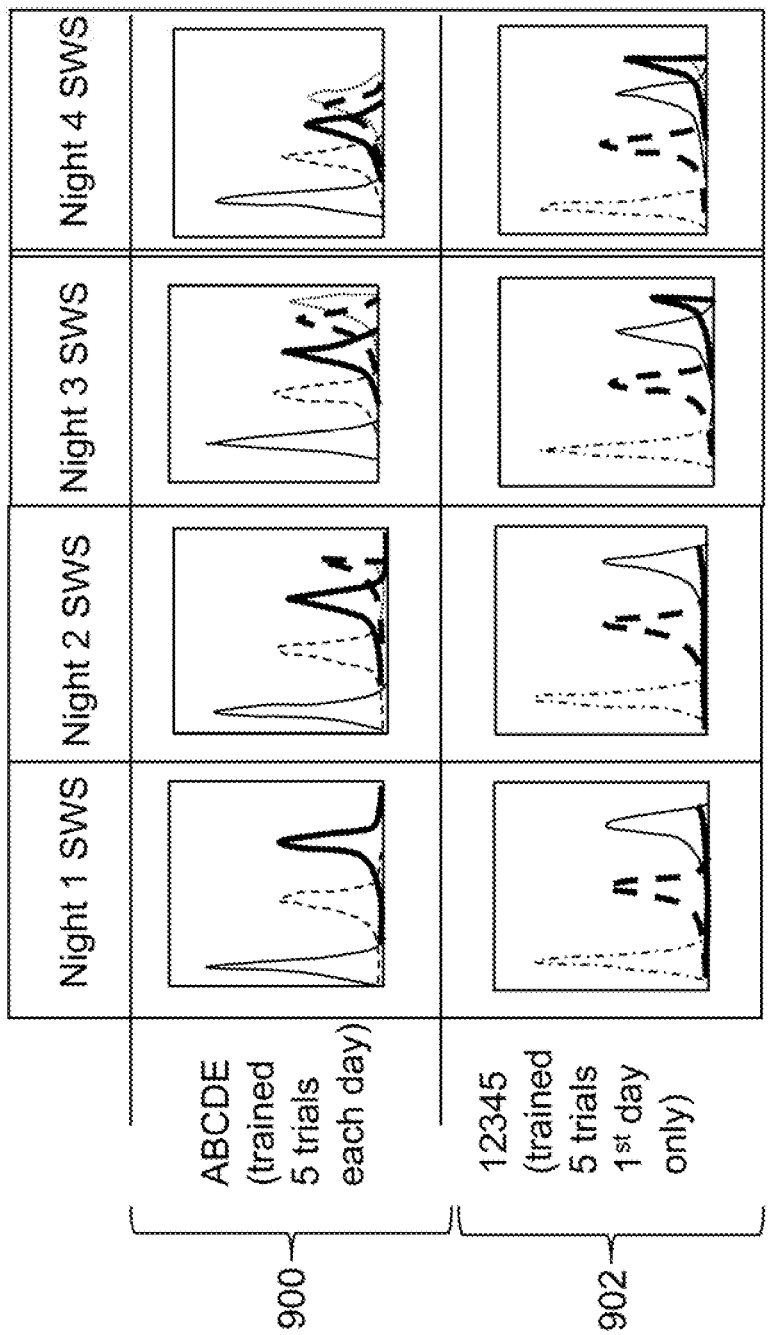
FIG. 9 is an illustration of representative replays of two separate sequences trained over 4 days and 4 nights according to some embodiments of the present disclosure.

Replays are modeled as a brief increase in activation, called a 'cue', of a single item randomly selected from a weighted distribution of recently active items taking place during the positive phase of the slow wave oscillation (the "UP state"). Due to the excitation caused by the connections between items, this results in sequential activations of other items that have been learned to be associated with the first. As a result, sequences that were presented multiple times during waking will be replayed whenever the first item of the sequence is cued. If a later item is cued, a partial sequence often replays starting from the cued item. As all replay activity must occur within the approximately 500 ms of the UP state, the temporal coefficient is increased during sleep, causing all rates of change to be increased. FIG. 9 depicts representative replays of two separate sequences 900 and 902 trained over 4 days and 4 nights. Each curve in each plot is the temporal activation level of one item in the sequence. For example, on night 1 in 900, the 3 curves are the level of item A as it becomes active and then dies out, and its activation is spread to item B neurons which become active (dotted curve) and then die down, and then to item C neurons that become active (bold line) and die down. In 902 night 1, the sequence 12345 is trained and the curves show item 1 then 2 then 3 in turn. The activations do cross over (it is hard to see in the drawing). One sequence (ABCDE) 900 is trained far more extensively than the other sequence 902 (4 nights training vs. 1) and as a result has significantly faster replays. This can be seen as the curves peak more closely together in time from night to night because the links between items are becoming stronger, thus activation spreads faster. Also, with stronger links the activation level spreads farther so during night 1 both sequences have their first 3 items activated, but on night 2 900 gets 4 items activated, and by night 3 all 5 items are activated. Sequence 900, which does not get as much training, never gets more than 4 items activated, and there is not as much speedup.

The item to be cued is selected from a weighted distribution, where the weight for each item is a factor called 'salience'. The salience factor of an item increases whenever a given item is active and decays over time. In each UP state, an item is selected to be cued, with selection probability proportional to the salience weight (i.e., how often it has been active in the recent past in comparison with other items). A "none" cue is represented in the distribution as well, meaning the probability that no replay will be cued. A fixed weight is assigned to the "none" cue. This results in a no cue probability that increases when no items have been active recently.

Because learning is still enabled during sleep, reactivated connections tend to increase their connection strengths. Additionally, because of the faster time scale of activation and the dependence of learning upon the rate of change of activation of the post synaptic cell, the rate of weight changes is considerably higher during replays. This is most important in the slower learning cortex. Sleep replays allow the connections in the cortex to become much stronger in a short period of time with no additional training.

(3.5) Waking Recall Metric

In sequence learning experiments, the model is trained on repeated exposures to sequences of events that are represented by letters or numbers. Performance improvement with each presentation of a training stimulus may be tracked by measuring the ability to recall. Below is a description of how the metric data collection and computation works (see equations (6) and (7)). The recall metric described below is a function of the activation levels of each item constituting the memory, and its ability to rise above the other activations going on at the same time (refer to the contrast and P in equations (6) and (7) below). In this way, the recall metric is used to predict behavioral performance based on strengths of memories in the neural model.

(3.5.1) Algorithm for the Recall Metric
a. Get activation history for the current recall, which is an array of current activations for each item (i.e., the activation of the item at each time point (dt) from the time when the recall is cued until all item activations return to zero, assuming no other events are perceived during this time period).
b. For each item, identify the time period that begins when the item's activation level becomes higher than the rest of the items, and ends when its level is surpassed by that of another item.
c. Compute the contrast of each item at each timestep with respect to the mean activations of every other item using equation (6).
d. Compute the mean value of contrast for each item i ( $\bar{c}_i$) during the times when its contrast is at a maximum.
e. Compute P using equation (7), which sums up the respective contrasts, with a factor added for permutation of the sequence ($|p_i|$, which is an edit distance of the recalled list from the trained list).

$$C_i(t) = \frac{a_i - \text{mean}(a_{j \neq i})}{a_i + \text{mean}(a_{j \neq i})} \quad (6)$$

$$P = \sum_i \frac{1}{N}\left(\frac{1}{|p_i|+1}\right)\bar{c}_i \quad (7)$$

$N$ = length (# items) of sequence
$i$ = index of an item in sequence
$ct_i$ = activation level of item $i$
$\bar{c}_i$ = mean contrast of item $i$
    during $1^{st}$ 200 ms of period when $c_i > c_k$,
$k \neq i$
$p$ = transposition error: difference between position of item in practiced sequence vs. position during $recallc_i(t)$ =
    contrast of item $i$ at time $t$ (amount $act_i(t)$)
        compared to mean ($act_{-i}(t)$))

The recall metric described herein considers an item as being recalled if its contrast rises above that of all the other items. FIGS. 10A and 10B show an example in short-term memory (hippocampus) of simulation of recall of a sequence of items A, B, C, D, after the sequence was trained and subsequently A is presented as a cue. Recall time is computed only on the subsequently recalled items in the sequence A, B, C, D. FIG. 10A plots the contrast $c_i(t)$ compared to the actual activation levels (shown in FIG. 10B) of each item as they are recalled. Contrast is computed over multiple 200 ms time windows. This technique is used to make behavioral predictions based on the training and sleep consolidation. The recall metric is based on item activations, but a simple averaging of weights between items could offer a reasonable prediction of recall ability as well.

(3.6) Experimental Studies

The neural model (FIG. 4, 302) exhibits key properties of memory, based on the literature. The properties include: practice increases speed of memory access and strength of recall; hippocampus (short-term memory 400) learns faster than cortex (long-term memory 402); contradictory inputs degrade the ability to recall the conflicting practiced items; complementary inputs don't degrade performance; and memory traces decay over time, faster in short-term memory than in long-term memory.

Using simulated inputs, the neural model simulates sequence learning (see FIGS. 9, 10A, and 10B). A paired associates task is another common experiment used in psychology and neuroscience in which two items are presented together, and when subsequently presented with one, the subject must recall the other. It can also be simulated in the neural model described herein, since it has the same properties as a two item sequence. In effect, a pair is a simultaneous sequence. In the experiment described below, the neural model's simulation of recall accuracy assessed by the metric described above is compared. The first ten exposures of the main sequence A-B-C-D-E is followed by another training session often exposures on one of four second sequences, including the same (A-B-C-D-E), contradictory (E-D-C-B-A), complementary (B-C-D), and part contradictory and part complementary (A-B-C-P-Q).

Figure 11B:
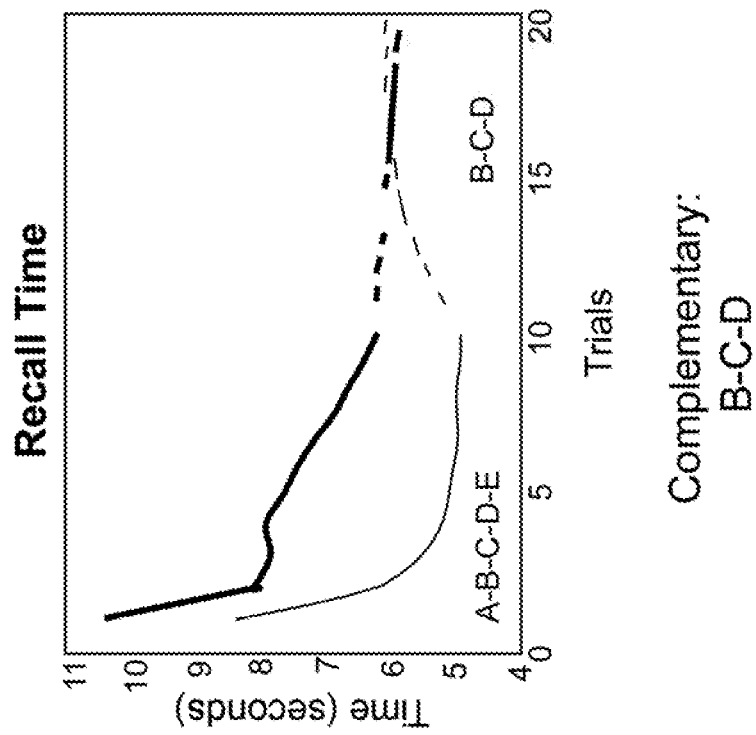
FIG. 11B is a plot of a recall time metric for a complementary condition according to some embodiments of the present disclosure.
Figure 11A:
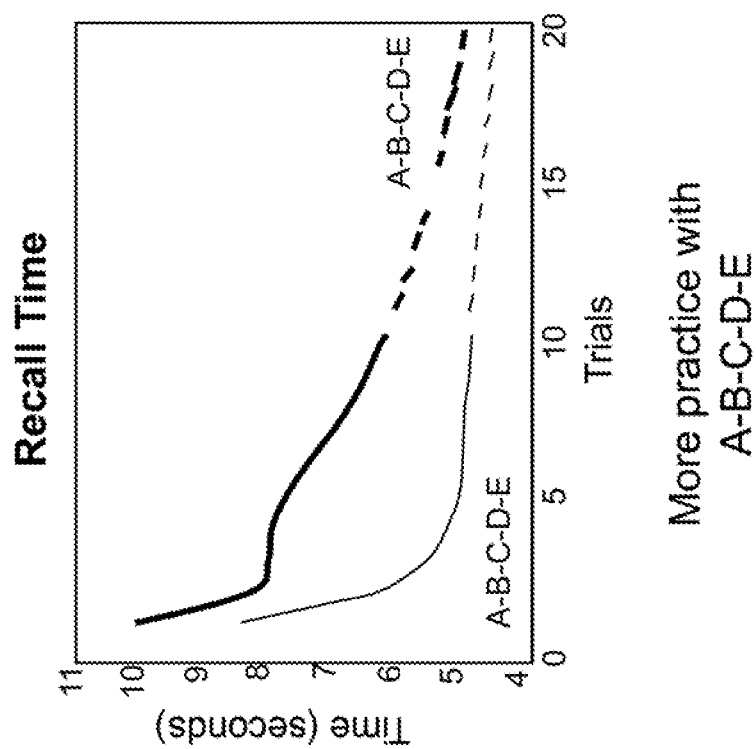
FIG. 11A is a plot of a recall time metric for a more practice condition according to some embodiments of the present disclosure.
Figure 11D:
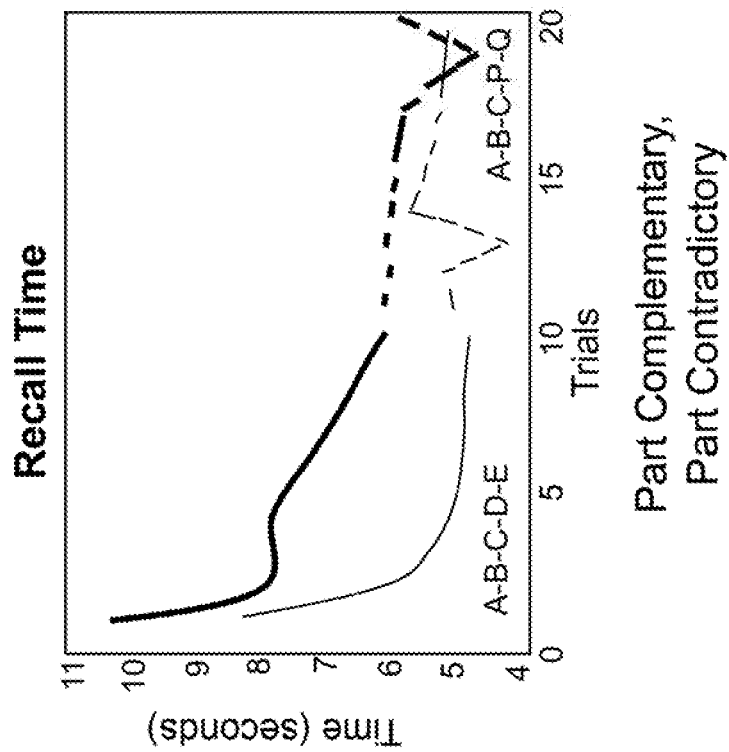
FIG. 11D is a plot of a recall time metric for a part complementary, part contradictory condition according to some embodiments of the present disclosure.
Figure 11C:
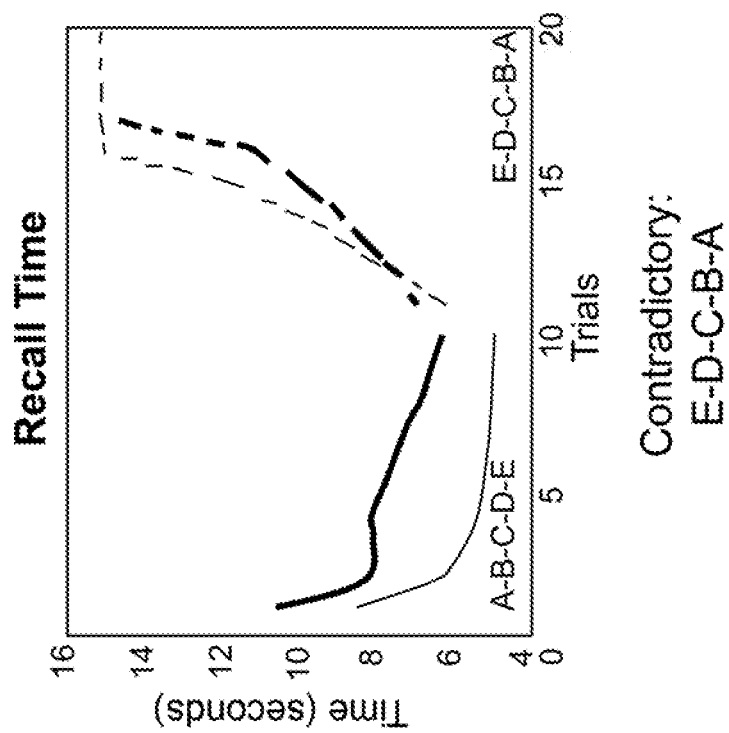
FIG. 11C is a plot of a recall time metric for a contradictory condition according to some embodiments of the present disclosure.

After each training session, the performance was tested by presenting "A" as a cue. The metric compared the recall cascade of item activations with the first practice sequence (A-B-C-D-E). This was only waking practice and testing; there was no sleep consolidation. FIGS. 11A-11D and 12A-12D illustrate the recall metric plotted for each of the four conditions described above: the same sequence, a complementary sequence, a contradictory sequence, and a mixed sequence. FIGS. 11A-11D depict the recall time metric plotted for each of four conditions. FIG. 11A is a plot of continued practice of the same sequence, FIG. 11B is a plot of a complementary sequence, FIG. 11C is a plot of a contradictory sequence, and FIG. 11D is a plot of a mixed sequence. In each of the plots, the unbolded line represents the hippocampus, and the bold line represents the cortex. Continued practice (FIG. 11A) lead to more improvement than other sequences. Contradictory sequences (FIG. 11C) actively reduced the model's performance. Partially complementary presentations (FIG. 11D) resulted in some performance improvement. In summary, practice increases speed of memory access, and contradictory items slow access.

Figure 12D:
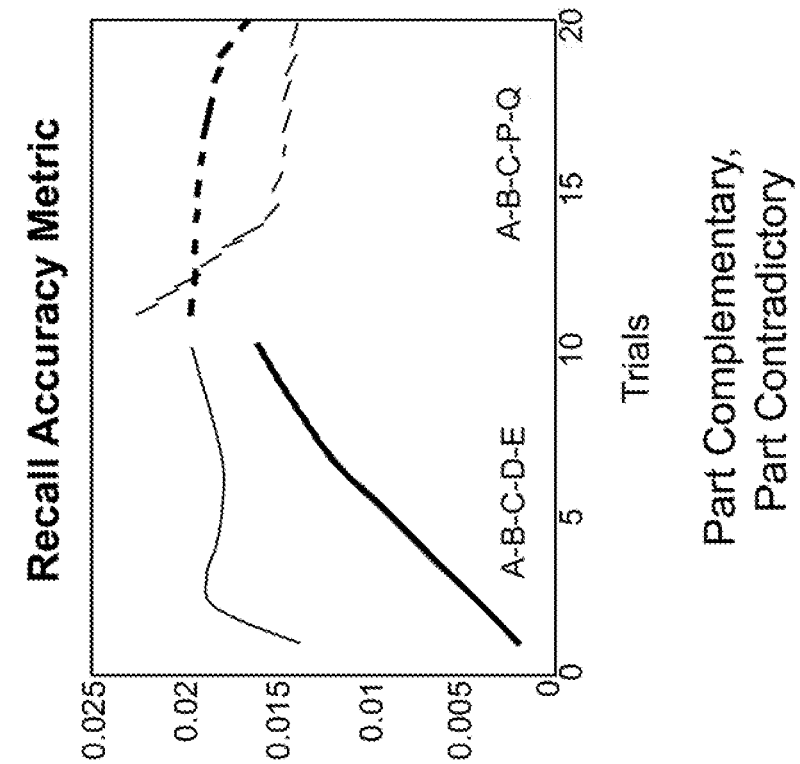
FIG. 12D is a plot of a recall accuracy metric for a part complementary, part contradictory condition according to some embodiments of the present disclosure.
Figure 12C:
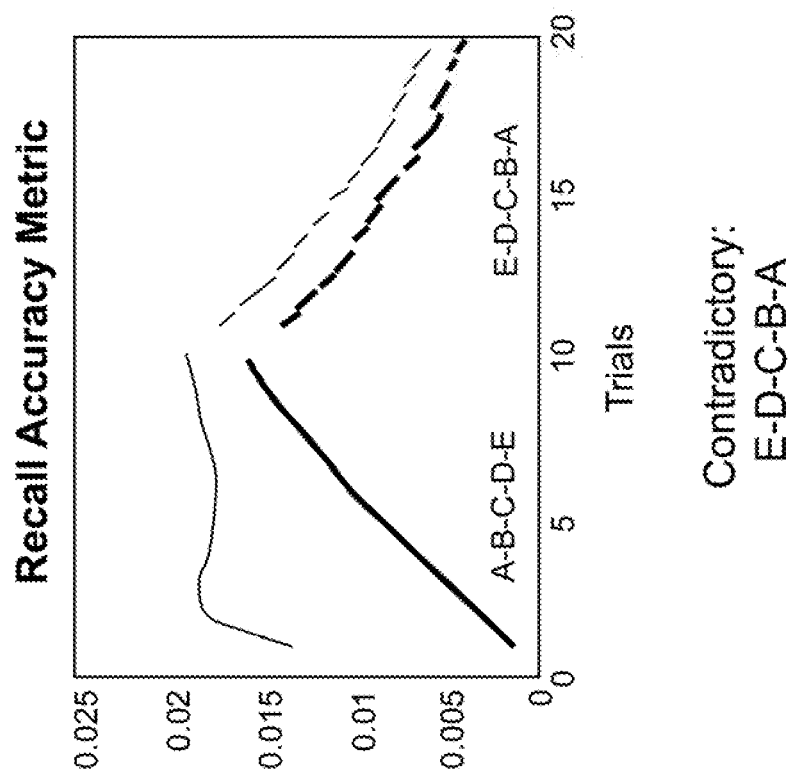
FIG. 12C is a plot of a recall accuracy metric for a contradictory condition according to some embodiments of the present disclosure.

FIGS. 12A-12D are plots of the recall accuracy metric plotted for the same sequence (FIG. 12A), a complementary sequence (FIG. 12B), a contradictory sequence (FIG. 12C), and a mixed sequence (FIG. 12D). In each of the plots, the unbolded line represents the hippocampus, and the bold line represents the cortex. Accuracy improves for continued training and complementary sequences, but degrades for contradictory sequences. In summary, practice increases the strength of recall. Contradictory information degrades the ability to recall practiced information. This could explain the decay of memory over longer time periods.

Figures 13A, 13B:
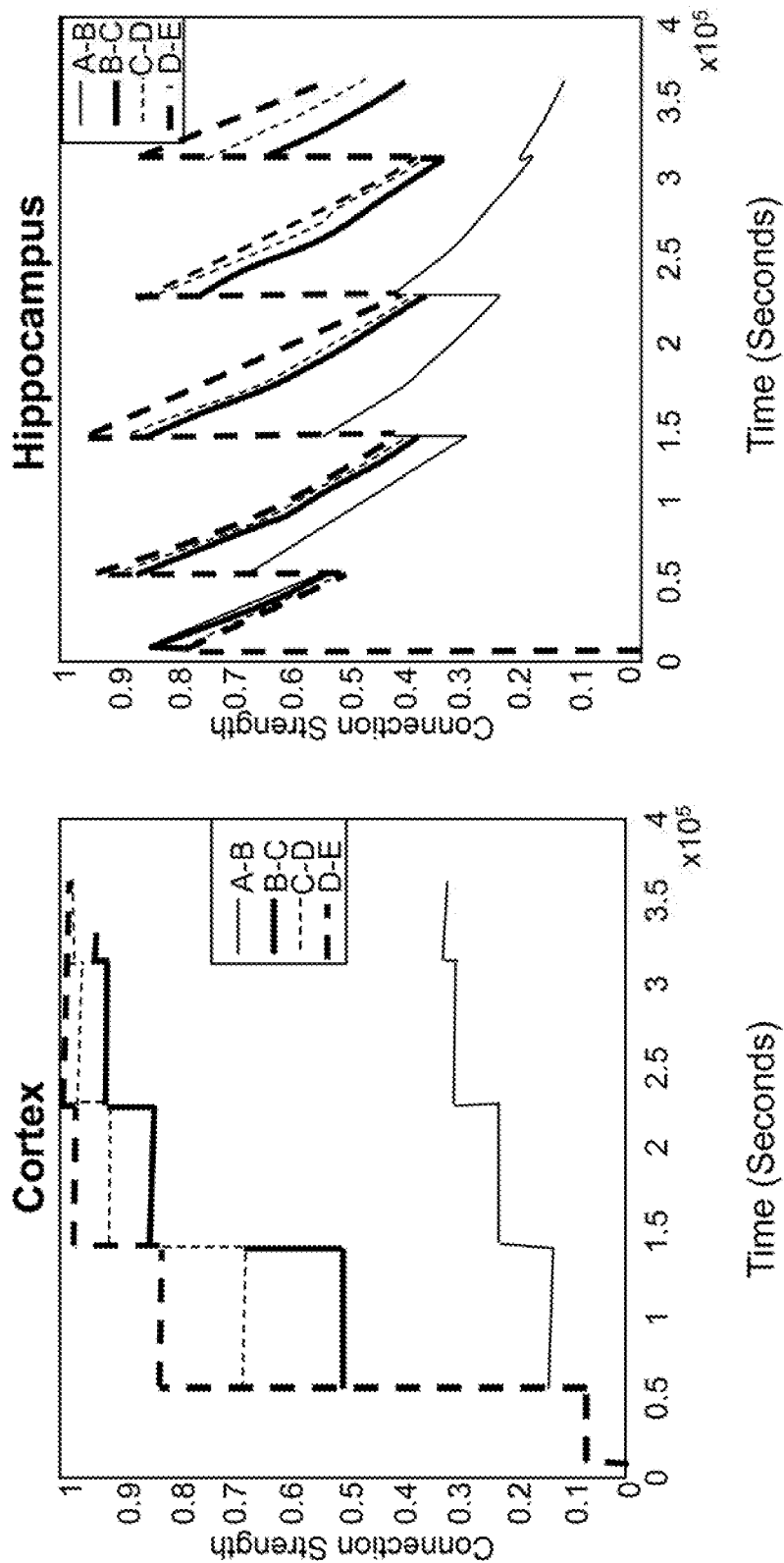
FIG. 13A is a plot of connection strength in the cortex without interference according to some embodiments of the present disclosure.
FIG. 13B is a plot of connection strength in the hippocampus without interference according to some embodiments of the present disclosure.

FIGS. 13A and 13B show how the weights between items in the short-term memory (cortex, FIG. 13A) and long-term memory (hippocampus, FIG. 13B) vary over 4 days after being initially trained without interference. Each night, the memories are reactivated in slow-wave-sleep, strengthening the weights in cortex (which decay over very long time scales). During the day, the short-term memory weights decay. Hippocampal feedback is maintained. Replays continue for all 4 days, and significant strength is developed in cortical connections.

Figures 13C, 13D:
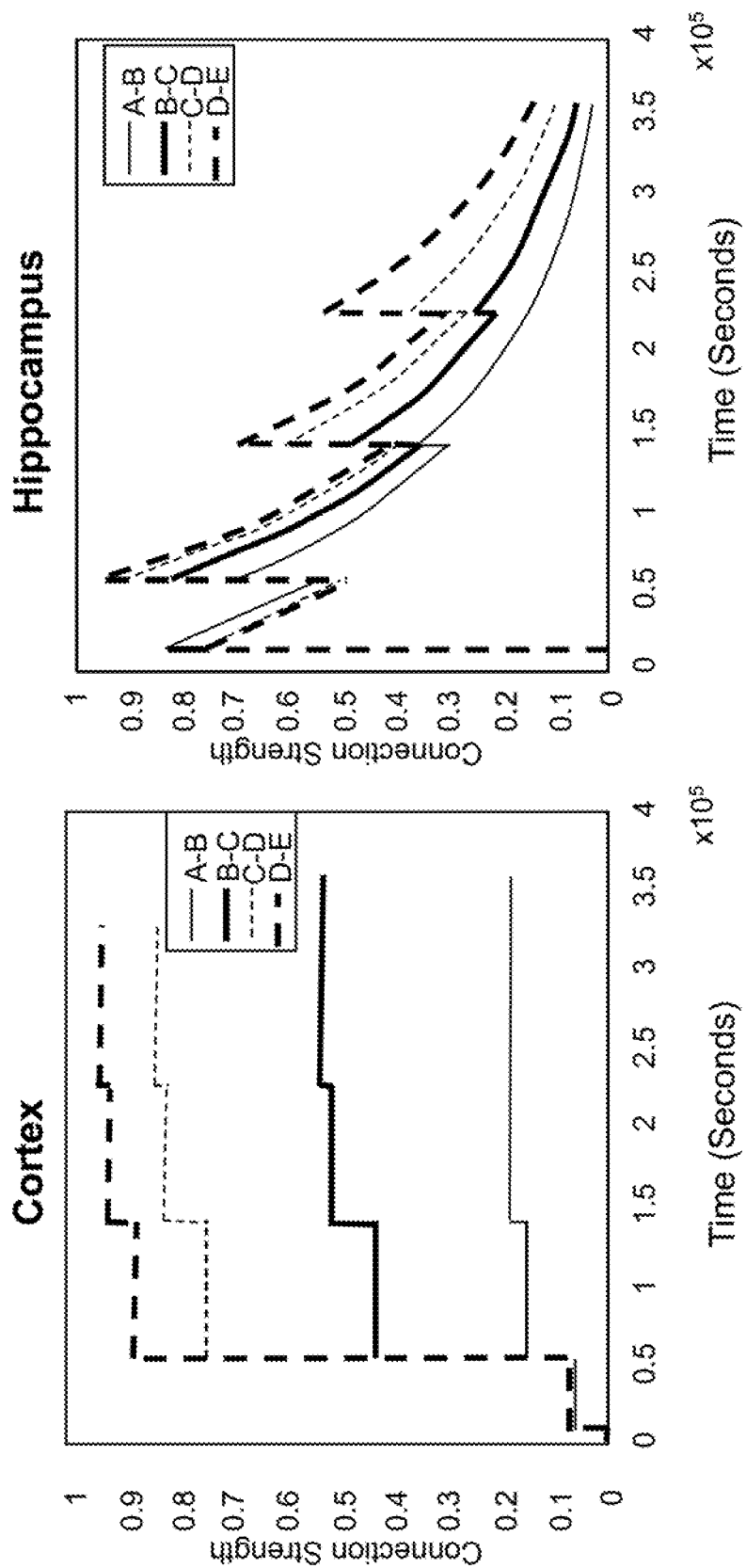
FIG. 13C is a plot of connection strength in the cortex with interference according to some embodiments of the present disclosure.
FIG. 13D is a plot of connection strength in the hippocampus with interference according to some embodiments of the present disclosure.

FIGS. 13C and 13D show the same plots for the case where contradictory interfering items are learned. FIG. 13C depicts short-term memory, and FIG. 13D depicts long-term memory. As shown, the decay is steeper, and the short term weights are learned more slowly. Hippocampal feedback is maintained. Interference reduces, then eliminates, replays. The plots show strong growth of cortical connections early on but very little in the second night and beyond.

The invention described herein makes possible, for the first time, a targeted personalized closed-loop system for enhancing memory in both normal subjects and those with learning difficulties related to memory consolidation. There are multiple applications for the invention of this disclosure. For instance, vehicle manufacturers could use the system for training, or as a commercial product. Since there is recent widespread interest into brain enhancement technologies, and there are several commercial systems on the market today, the control technique system according to embodiments of the present disclosure can be incorporated into a product and reach the market in the near future. For example, the closed-loop model-based control of interventions can be incorporated into the products of companies that stimulate and treat the brain.

This invention makes behavioral predictions by computing a recall metric based on the weights of the memories. This recall metric can be mapped to actual performance metrics of particular subjects by adding a readout model, as described in U.S. Provisional Application No. 62/570,663, which is hereby incorporated by reference as though fully set forth herein.

The prior art memory intervention techniques described in Literature Reference Nos. 1, 2, and 3 were only tested in a laboratory, under supervised sleep conditions. They were never intended for real-world use; only for research on memory consolidation. Whether in the laboratory or in real-world settings, there exists no method to control which particular memories need to be enhanced, or to stop the intervention for a particular memory when it has been enhanced sufficiently, to allow other memories to consolidate. To provide such control over specific memory enhancement interventions in the laboratory, and to make this into a commercial product that could be used by individuals apart from a supervised laboratory setting, the intervention delivery system must be automated. That is because, while the subject is in slow-wave sleep or any other cognitive state when memory replays occur, EEG must be analyzed in real time (within the slow-wave oscillation half cycle) to decide which memory intervention should be applied in the next cycle, if at all. No human supervisor can make these determinations as fast as an automated system, and without waking up the subject for performance testing. The purpose of the present invention is to add such automation, making these approaches efficient and effective by assessing the subject's brain state and predicting in real time when to apply the intervention.

Products resulting from this disclosure will enable people to reinforce episodic memories and acquire skills faster, while they sleep. The system, when appropriately paired with a memory consolidation technique, could be an enormous commercial success, since it automates some of the supervision required to use the technique. Thus, the invention is part of the transition to move these techniques out of clinical settings and into home use.

Additionally, the model described herein will also prove exceedingly useful in a pedagogical automated system, such as teaching and training software. Having a more accurate assessment of information retained by the user will allow such software to focus on the areas of learning where additional training will be the most useful. Furthermore, missions such as surveillance and after-mission debriefs require detailed memories that can be enhanced and clarified by the system according to embodiments of this disclosure, which can accelerate mission rehearsal time.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for memory improvement intervention, the system comprising:
 one or more processors and a non-transitory computer-readable medium having executable instructions encoded thereon such that when executed, the one or more processors perform operations of:
 during a waking state, recording a plurality of biometric values of a person while the person is experiencing a specific memory;
 incorporating the plurality of biometric values into a neural memory model:
 using the neural memory model, generating a performance prediction for recall of the specific memory;
 receiving and analyzing real-time electroencephalogram (EEG) signals of the person to detect a sleep state;
 if the performance prediction is below a first threshold, then using a memory enhancement intervention system, applying an intervention during the detected sleep state to improve consolidation of the specific memory; and
 if the performance prediction is below a second threshold, reducing the intervention performed using the memory enhancement intervention system.

2. The system as set forth in claim 1, the system further comprising:
 a plurality of brain sensors to provide the real-time EEG signals; and
 the memory enhancement intervention system, wherein the neural model is part of a closed-loop control system.

3. The system as set forth in claim 1, wherein a recall metric is used to generate the performance prediction based on strengths of memories in the neural memory model.

4. The system as set forth in claim 3, wherein the first threshold and second threshold are values of the recall metric.

5. The system as set forth in claim 1, wherein the system controls intervention that applies to the specific memory such that consolidation of other memories is also allowed to occur.

6. The system as set forth in claim 1, wherein the neural memory model comprises a short-term memory store and a long-term memory store, wherein each memory store comprises a plurality of items, each item having an activation level that evolves dynamically over time, wherein while an item is active, it forms links with other items that are active at the same time, wherein the links are directional to represent an order in which the linked items are experienced.

7. The system as set forth in claim 6, wherein the links are represented as weight values, and wherein weight values are updated based on the activation levels of the linked items.

8. The system as set forth in claim 6, wherein recall is a function of the activation level of each item, wherein each item is considered recalled if its activation level rises above the other activations going on at the same time.

9. A computer implemented method for memory improvement intervention, the method comprising an act of:
causing one or more processers to execute instructions encoded on a non-transitory computer-readable medium, such that upon execution, the one or more processors perform operations of:
during a waking state, recording a plurality of biometric values of a person while the person is experiencing a specific memory;
incorporating the plurality of biometric values into a neural memory model;
using the neural memory model, generating a performance prediction for recall of the specific memory;
receiving and analyzing real-time electroencephalogram (EEG) signals of the person to detect a sleep state;
if the performance prediction is below a first threshold, then using a memory enhancement intervention system, applying an intervention during the detected sleep state to improve consolidation of the specific memory; and
if the performance prediction is below a second threshold, reducing the intervention performed using the memory enhancement intervention system.

10. The method as set forth in claim 9, wherein a recall metric is used to generate the performance prediction based on strengths of memories in the neural memory model.

11. The method as set forth in claim 10, wherein the first threshold and second threshold are values of the recall metric.

12. The method as set forth in claim 9, wherein the system controls intervention that applies to the specific memory such that consolidation of other memories is also allowed to occur.

13. The method as set forth in claim 9, wherein the neural memory model comprises a short-term memory store and a long-term memory store, wherein each memory store comprises a plurality of items, each item having an activation level that evolves dynamically over time, wherein while an item is active, it forms links with other items that are active at the same time, wherein the links are directional to represent an order in which the linked items are experienced.

14. The method as set forth in claim 13, wherein the links are represented as weight values, and wherein weight values are updated based on the activation levels of the linked items.

15. The method as set forth in claim 13, wherein recall is a function of the activation level of each item, wherein an item is considered recalled if its activation level rises above the other activations going on at the same time.

16. A computer program product for memory improvement intervention, the computer program product comprising:
computer-readable instructions stored on a non-transitory computer-readable medium that are executable by a computer having one or more processors for causing the processor to perform operations of:
during a waking state, recording a plurality of biometric values of a person while the person is experiencing a specific memory;
incorporating the plurality of biometric values into a neural memory model;
using the neural memory model, generating a performance prediction for recall of the specific memory;
receiving and analyzing real-time electroencephalogram (EEG) signals of the person to detect a sleep state;
if the performance prediction is below a first threshold, then using a memory enhancement intervention system, applying an intervention during the detected sleep state to improve consolidation of the specific memory; and
if the performance prediction is below a second threshold, reducing the intervention performed using the memory enhancement intervention system.

17. The computer program product as set forth in claim 16, wherein a recall metric is used to generate the performance prediction based on strengths of memories in the neural memory model.

18. The computer program product as set forth in claim 17, wherein the first threshold and second threshold are values of the recall metric.

19. The computer program product as set forth in claim 16, wherein the system controls intervention that applies to the specific memory such that consolidation of other memories is also allowed to occur.

20. The computer program product as set forth in claim 16, wherein the neural memory model comprises a short-term memory store and a long-term memory store, wherein each memory store comprises a plurality of items, each item having an activation level that evolves dynamically over time, wherein while an item is active, it forms links with other items that are active at the same time, wherein the links are directional to represent an order in which the linked items are experienced.

21. The computer program product as set forth in claim 20, wherein the links are represented as weight values, and wherein weight values are updated based on the activation levels of the linked items.

22. The computer program product as set forth in claim 20, wherein recall is a function of the activation level of each item, wherein each item is considered recalled if its activation level rises above the other activations going on at the same time.

* * * * *